US007613336B2

(12) United States Patent
Schultz

(10) Patent No.: US 7,613,336 B2
(45) Date of Patent: *Nov. 3, 2009

(54) METHODS AND APPARATUS FOR IMAGE RECOGNITION AND DICTATION

(76) Inventor: Leonard S. Schultz, 11036 Boone Cir. South, Bloomington, MN (US) 55438

( * ) Notice: Subject to any disclaimer, the term of this patent is extended or adjusted under 35 U.S.C. 154(b) by 0 days.

This patent is subject to a terminal disclaimer.

(21) Appl. No.: 10/827,558

(22) Filed: Apr. 19, 2004

(65) Prior Publication Data

US 2004/0197018 A1 Oct. 7, 2004

Related U.S. Application Data

(63) Continuation of application No. 09/860,728, filed on May 18, 2001, now Pat. No. 6,735,329.

(30) Foreign Application Priority Data

May 16, 2002 (US) .................... PCT/US02/15545

(51) Int. Cl.
*G06K 9/00* (2006.01)
(52) U.S. Cl. .................... 382/128; 382/112; 382/218; 382/278
(58) Field of Classification Search ............ 382/128, 382/209, 109, 112, 113, 278, 218
See application file for complete search history.

(56) References Cited

U.S. PATENT DOCUMENTS

| 4,881,270 A | 11/1989 | Knecht et al. |
| 4,996,707 A | 2/1991 | O'Malley et al. |
| 5,031,228 A | 7/1991 | Lu |
| 5,050,220 A | 9/1991 | Marsh et al. |
| 5,241,472 A | 8/1993 | Gur et al. |
| 5,261,404 A | 11/1993 | Mick et al. |
| 5,531,520 A | 7/1996 | Grimson et al. |
| 5,586,171 A | 12/1996 | McAllister et al. |
| 5,668,897 A * | 9/1997 | Stolfo .................... 382/283 |
| 5,682,330 A | 10/1997 | Seaman et al. |
| 5,704,371 A | 1/1998 | Shepard |
| 5,740,802 A | 4/1998 | Nafis et al. |

(Continued)

FOREIGN PATENT DOCUMENTS

WO      WO 01/18739      3/2001

(Continued)

OTHER PUBLICATIONS

Will computers replace transcriptionists?, *Medical Economics*, p. 111, Oct. 11, 1999.

(Continued)

*Primary Examiner*—Wesley Tucker
(74) *Attorney, Agent, or Firm*—David E. Bruhn; Dorsey & Whitney LLP

(57) ABSTRACT

The present invention relates to methods of and apparatus for producing and digitizing a number of images to create a digital library of images, providing an image from outside the digital library, digitizing it and comparing it to the digital images in the digital library, and providing a text descriptive of the image from outside the digital library.

30 Claims, 22 Drawing Sheets
(18 of 22 Drawing Sheet(s) Filed in Color)

U.S. PATENT DOCUMENTS

| | | | |
|---|---|---|---|
| 5,803,914 | A | 9/1998 | Ryals et al. |
| 5,832,450 | A | 11/1998 | Myers et al. |
| 5,951,571 | A | 9/1999 | Audette |
| 5,961,456 | A | 10/1999 | Gildenberg |
| 5,970,499 | A | 10/1999 | Smith et al. |
| 5,974,201 | A | 10/1999 | Chang et al. |
| 5,993,001 | A | 11/1999 | Bursell et al. |
| 6,002,798 | A * | 12/1999 | Palmer et al. ............... 382/176 |
| 6,024,695 | A | 2/2000 | Taylor et al. |
| 6,026,363 | A | 2/2000 | Shepard |
| 6,031,526 | A * | 2/2000 | Shipp ......................... 715/201 |
| 6,055,326 | A | 4/2000 | Chang et al. |
| 6,128,002 | A | 10/2000 | Leiper |
| 6,253,210 | B1 * | 6/2001 | Smith et al. .............. 707/104.1 |
| 6,397,213 | B1 * | 5/2002 | Cullen et al. ................... 707/5 |
| 6,415,048 | B1 | 7/2002 | Schneider |
| 6,488,627 | B1 | 12/2002 | Kim |
| 6,529,617 | B1 * | 3/2003 | Prokoski ..................... 382/128 |
| 6,735,329 | B2 | 5/2004 | Schultz |
| 6,804,684 | B2 * | 10/2004 | Stubler et al. ............ 707/104.1 |
| 2001/0043729 | A1 | 11/2001 | Giger et al. |
| 2002/0065460 | A1 | 5/2002 | Murao |
| 2002/0188602 | A1 * | 12/2002 | Stubler et al. .................. 707/3 |

FOREIGN PATENT DOCUMENTS

| | | |
|---|---|---|
| WO | WO 01/24050 | 4/2001 |

OTHER PUBLICATIONS

Todd, Joanne M., Dictating the Future, *healthcarebusiness*, 6 pages, Jul./Aug. 1999; http://www.healthcarebusiness.com/archives/healthcarebusiness/0799/20.html.

Terry, Ken. Instant patient records—and all you have to do is talk, *Medical Economics*, pp. 101-115, Oct. 11, 1999.

Voice Recognition Can Ease the Pain of Transcribing Patient Notes, *Practice Management advisor for the healthcare professional*, p. 2., Fall 1999.

Sanders, Darcy, abstracted by Elizabeth "Biff" De Silva, *Applying Smart Software to the Medical Field*, http://www.csubak.edu/hulpke/Tech/number12.html, Jan. 1, 2000 printed.

The Computer Vision Homepage, http://www.cs.cmu.edu/, 3 pgs., Oct. 14, 1999 last updated.

Artificial Intelligence, Robotics, and Vision Laboratory University of Minnesota, http://www.cs.umn.edu/Research/airvl, 2 pgs., Feb. 1, 2000 printed.

The Yale Vision and Robotics Group, http:/www.cs.yale.edu/VISION/GroupPR.html, 6 pgs., Jan. 27, 2000 printed. Journal of Biomedical Optics, editor list.

Datacube, Inc., datacube.com, Feb. 22, 2000 printed.

SpeechMachines, http://www.cybertrancriber.com/AboutUs/, homepage, about us, 2 pgs., Jun. 21, 2001 printed.

MedQuist, http:/www.medquist.com/, homepage, products, 2 pgs, Jun. 21, 2001 printed.

Dragon Systems, Inc., http:/www.voicerecognition.com/products/dragon, products index, 3 pgs., Jun. 21, 2001 printed.

IBM, http://imb.com,/software/speech, homepage, voice systems, ViaVoice for Windows, 4 pgs., Jun. 21, 2001 printed.

Lernout & Hauspie, http:/www/lhsl./com/default2.html, homepage, Voice Xpress, 2 pgs., Jun. 21, 2001 printed.

cMore Medical, http://www.cmoremedical.com/,homepage, products, Provalent, cMore GI, 4 pgs., Jun. 21, 2001 printed.

cMore Medical, http://www.cmoremedical.com/, company background, our software products, careers, 7 pgs., Dec. 9, 1999 printed.

* cited by examiner

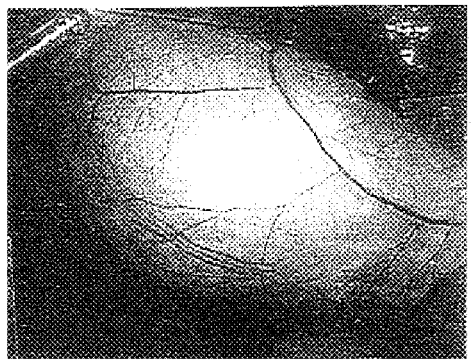
FIG. 1a
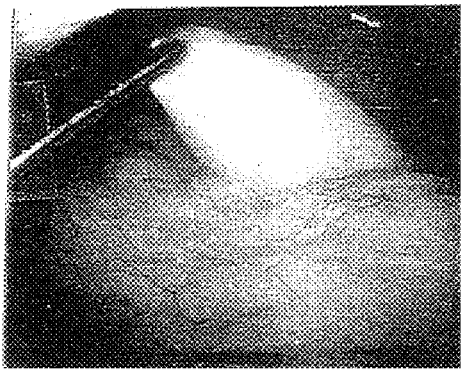
FIG. 1b
FIG. 1c
FIG. 1d
FIG. 1e
FIG. 1

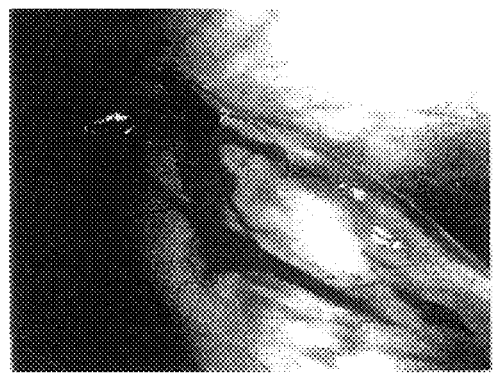
FIG. 2a
FIG. 2b
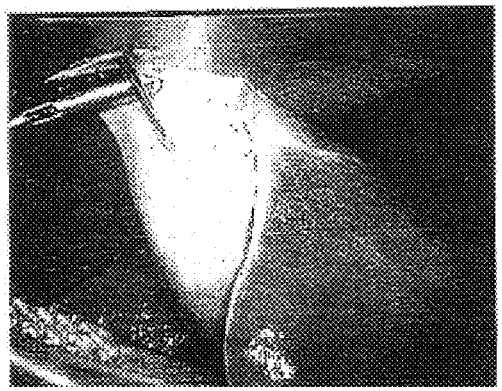
FIG. 2c
FIG. 2

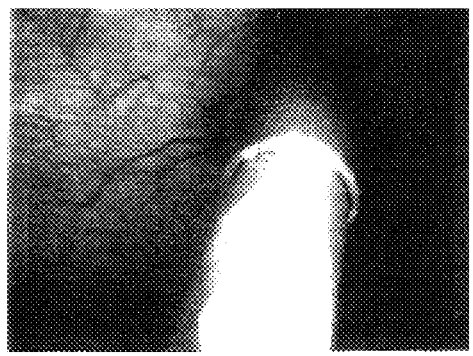
FIG. 3a
FIG. 3b
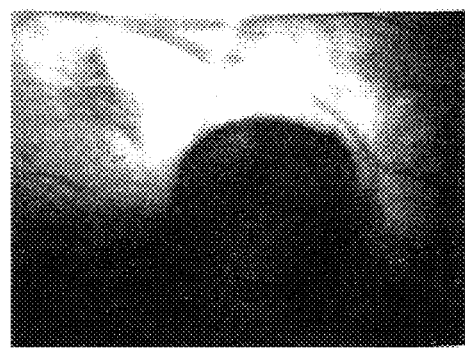
FIG. 3c
FIG. 3d
FIG. 3

FIG. 4a
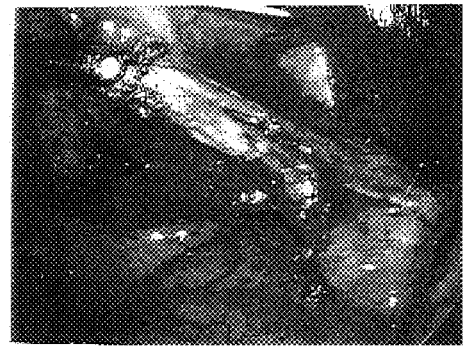
FIG. 4b
FIG. 4c
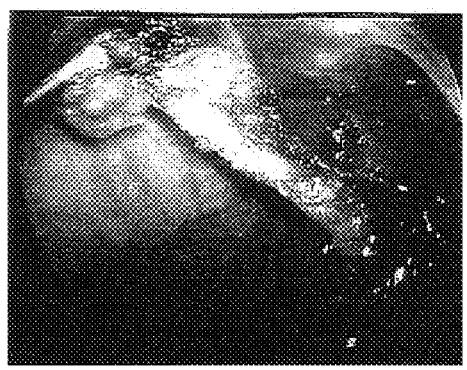
FIG. 4d
FIG. 4

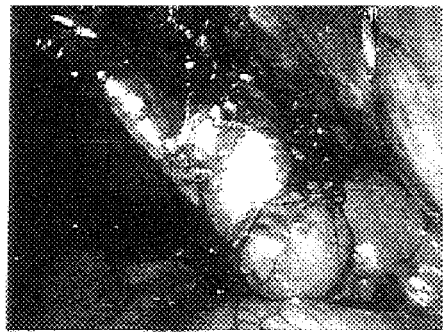
FIG. 4e
FIG. 4f
FIG. 4g
FIG. 4h
FIG. 4i
FIG. 4

FIG. 5
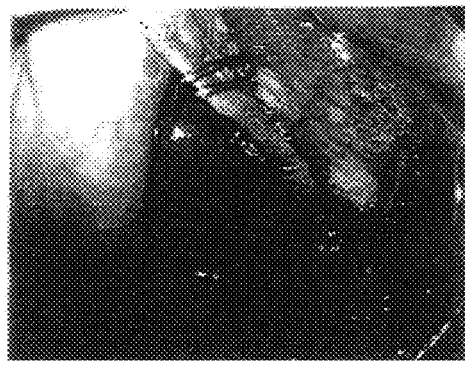
FIG. 5a
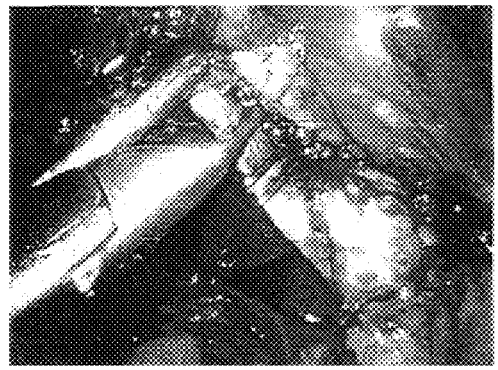
FIG. 5b
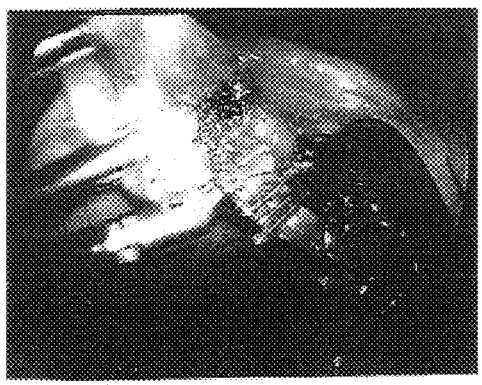
FIG. 5c
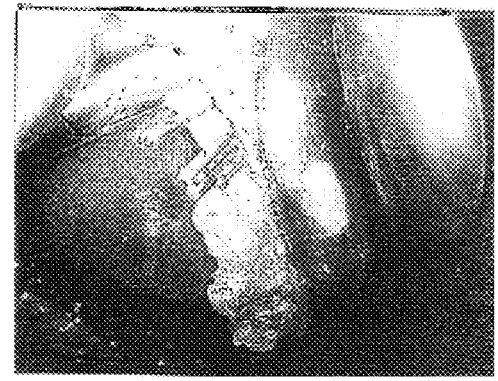
FIG. 5d
FIG. 5e
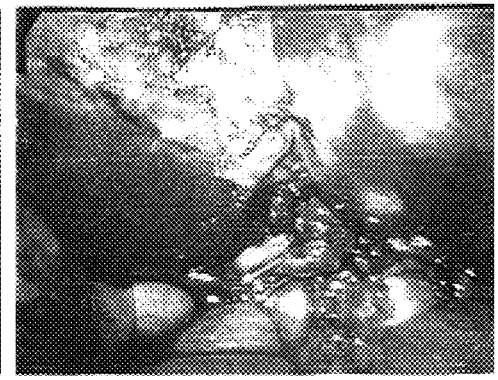
FIG. 5f

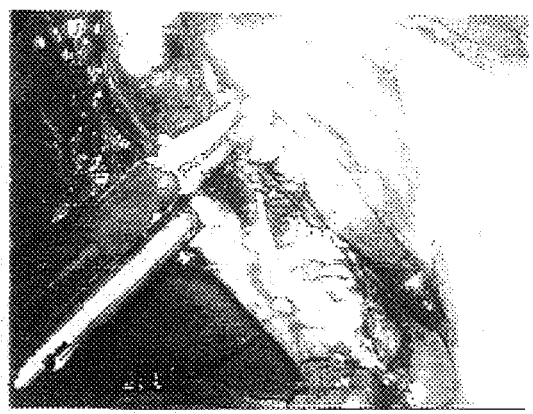
FIG. 6a
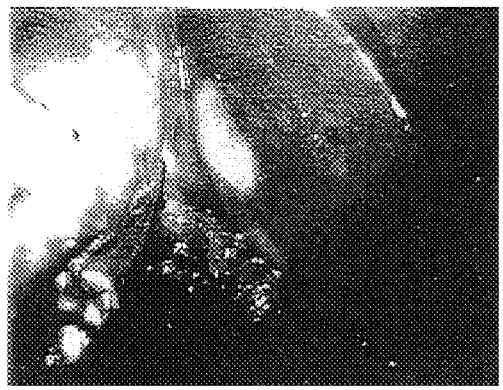
FIG. 6b
FIG. 6
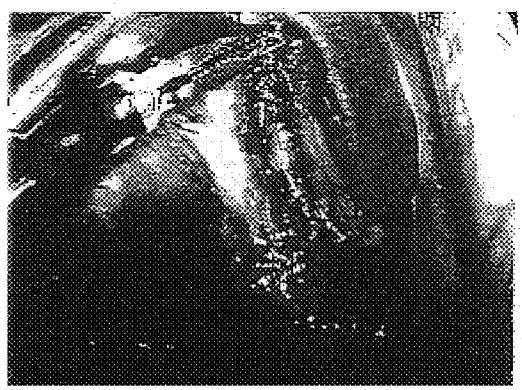
FIG. 6c

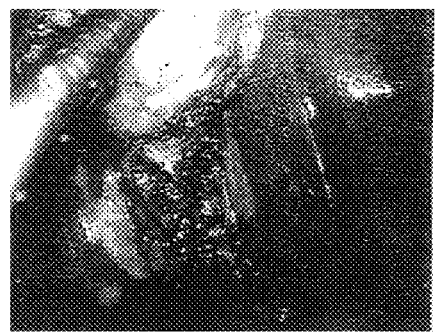
FIG. 7a
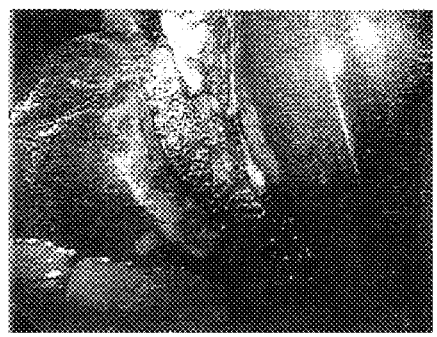
FIG. 7b
FIG. 7c
FIG. 7d
FIG. 7

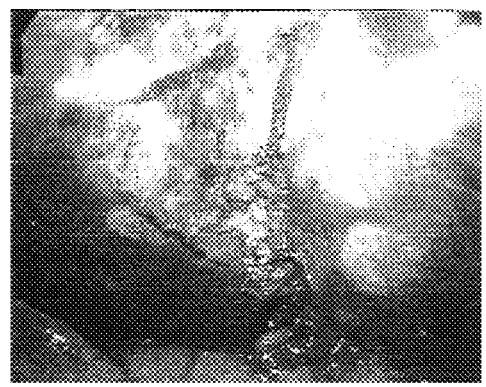
FIG. 7e
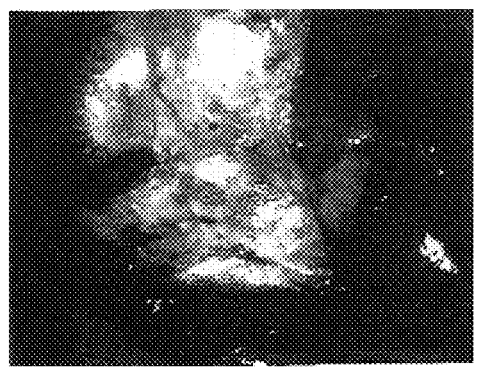
FIG. 7f
FIG. 7
FIG. 7g

FIG. 8a
FIG. 8
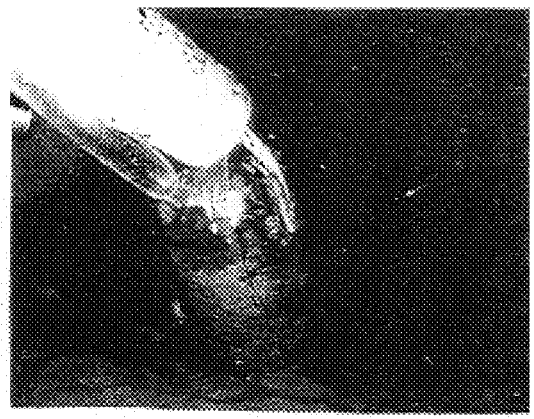
FIG. 8b

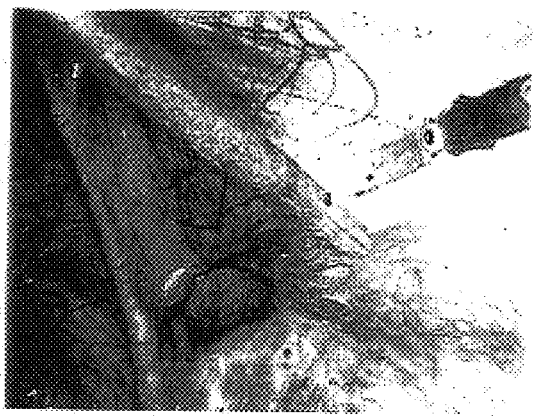
FIG. 9a
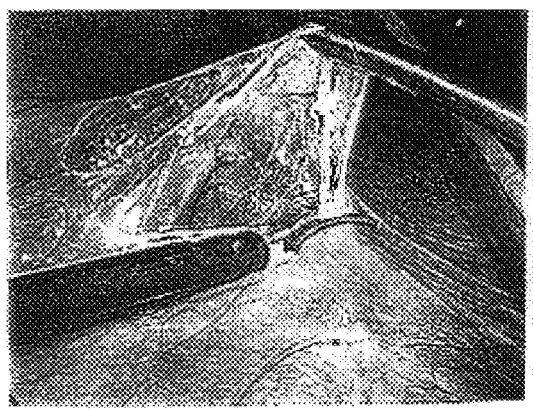
FIG. 9
FIG. 9b
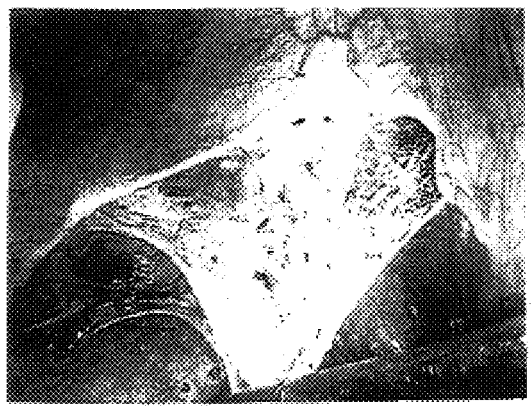
FIG. 9c

FIG. 10
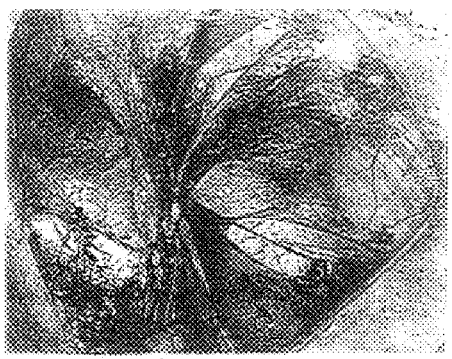
FIG. 10a
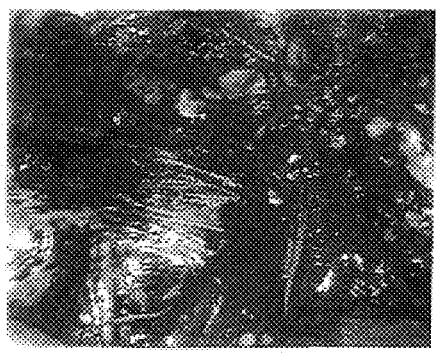
FIG. 10b
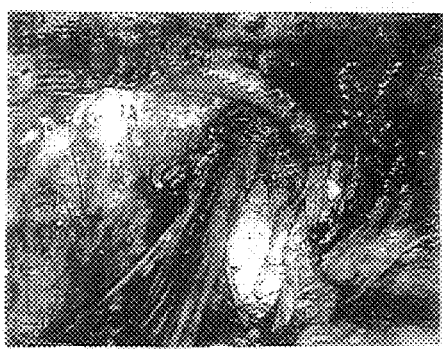
FIG. 10c
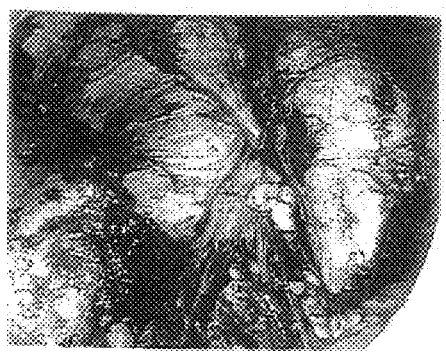
FIG. 10d
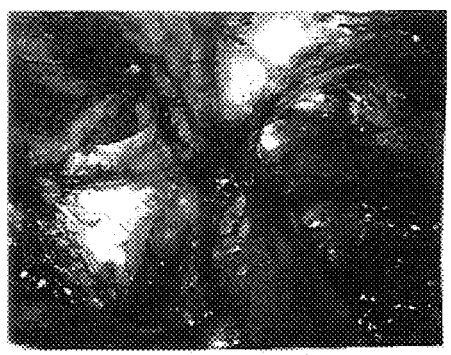
FIG. 10e
FIG. 10f

FIG. 10g
FIG. 10h
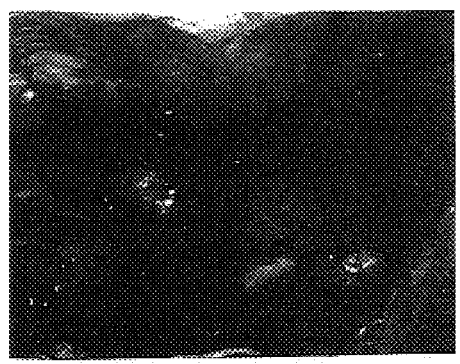
FIG. 10i
FIG. 10

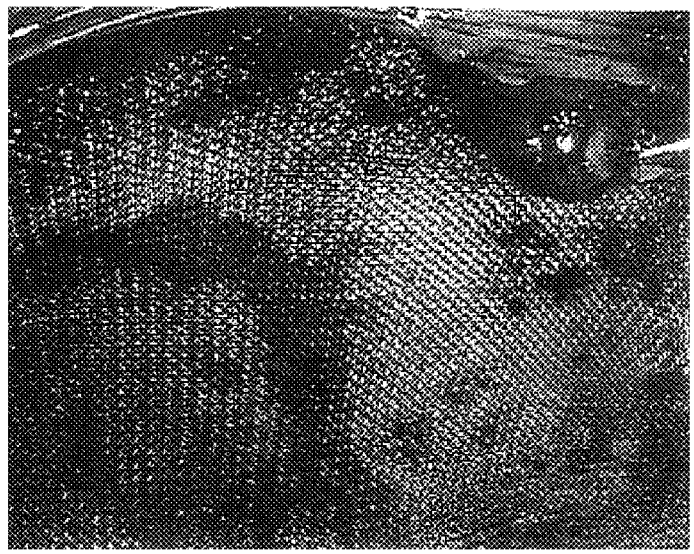
FIG. 11a
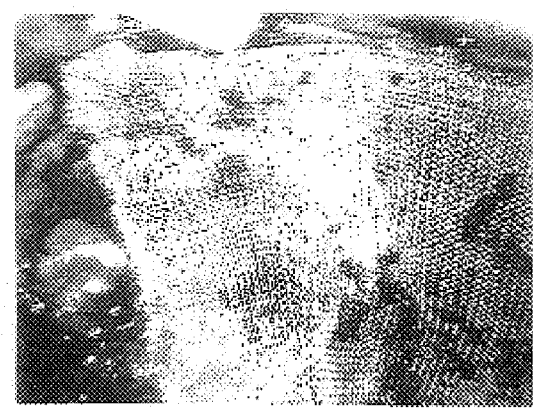
FIG. 11b
FIG. 11

FIG. 11c
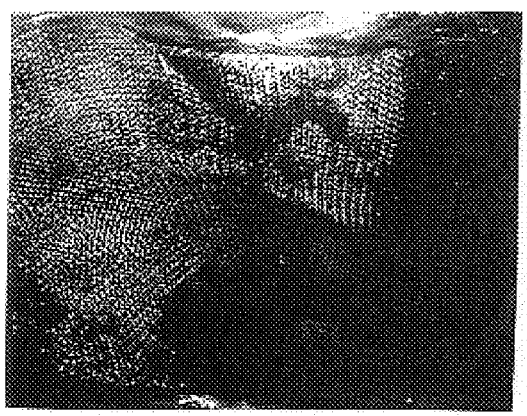
FIG. 11d
FIG. 11
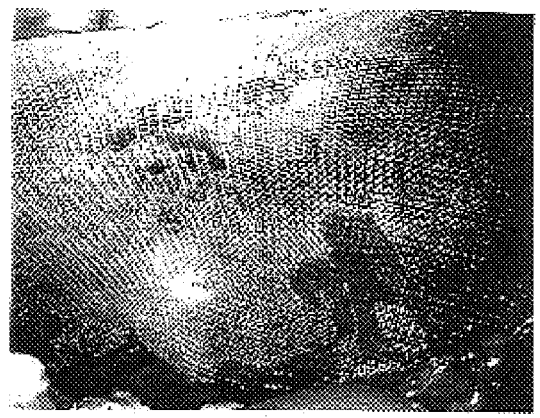
FIG. 11e

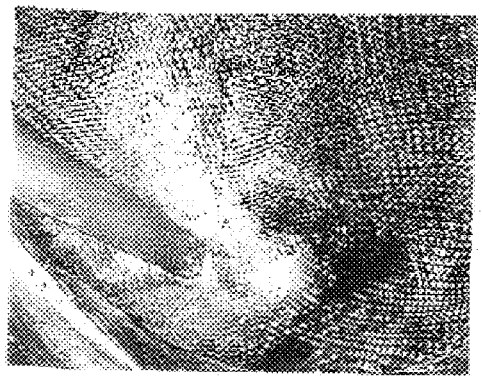
FIG. 12a
FIG. 12b
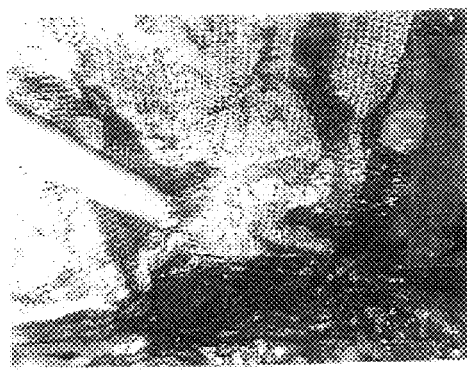
FIG. 12c
FIG. 12d
FIG. 12
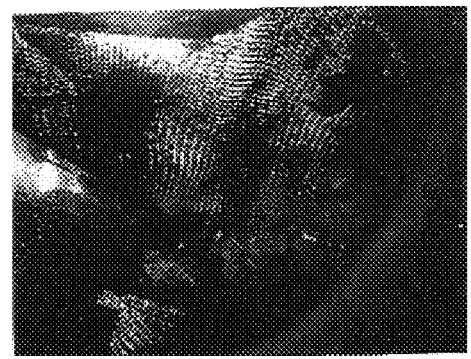
FIG. 12e FIG. 13
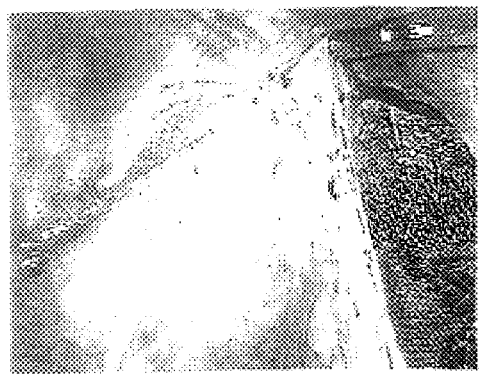
FIG. 13a
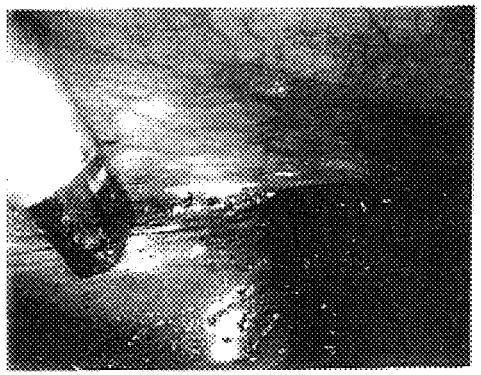
FIG. 13b
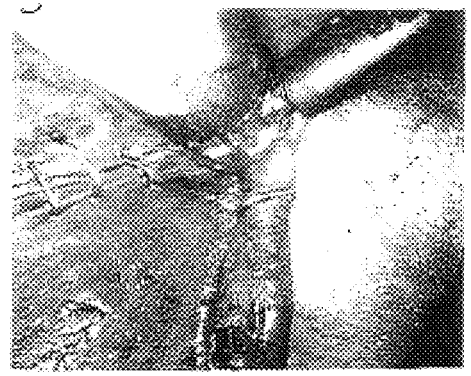
FIG. 13c
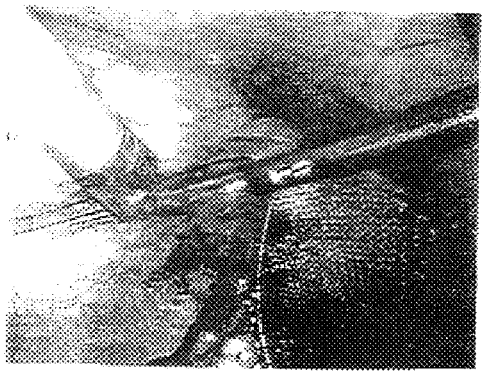
FIG. 13d
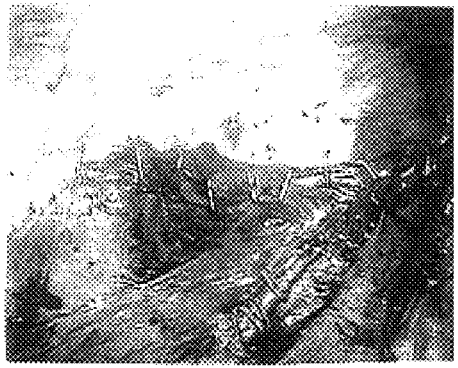
FIG. 13e
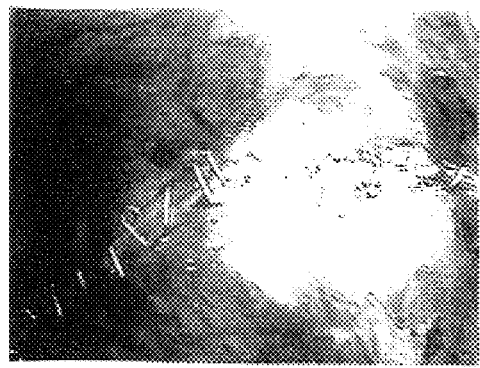
FIG. 13f

FIG. 13g
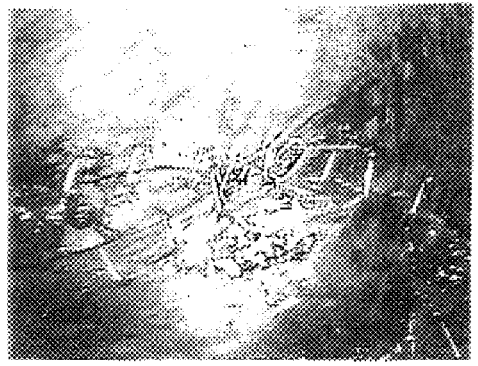
FIG. 13h
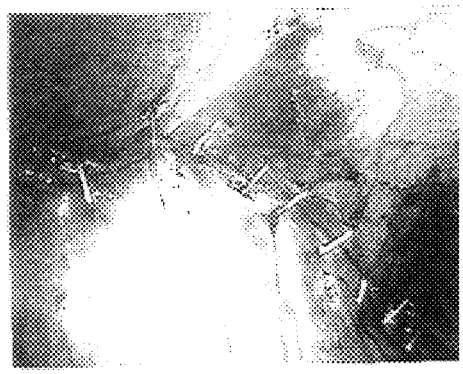
FIG. 13i
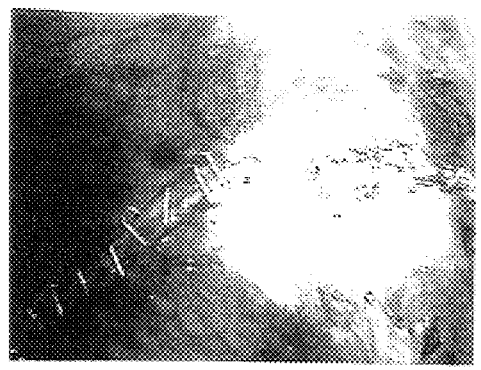
FIG. 13j
FIG. 13

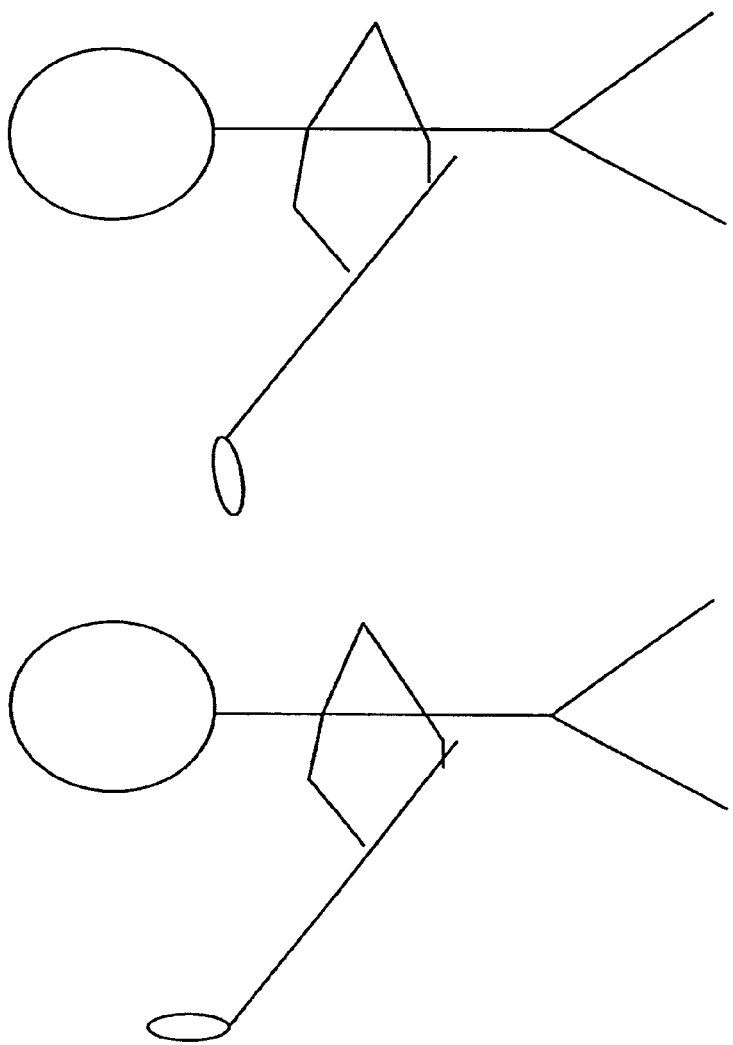
FIG 16: Library of Figures for Back Swing

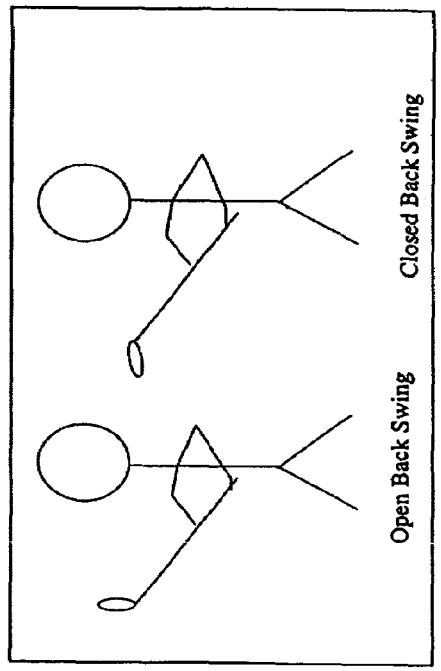
FIG. 17: Comparison of Obtained Image to Image Library to Generate Report

METHODS AND APPARATUS FOR IMAGE RECOGNITION AND DICTATION

CROSS REFERENCE TO RELATED APPLICATIONS

This application is a continuation of U.S. patent application Ser. No. 09/860,728, filed May 18, 2001, now U.S. Pat. No. 6,735,329, issued May 11, 2004, and claims priority to international application PCT/US02/15545, filed May 16, 2002, all of which are incorporated herein by reference in their entirety.

BACKGROUND

The present invention relates to methods of and apparatus for making a history or record, particularly, but not exclusively, of medical treatments or procedures, and to methods of and apparatus for using the history or record. More particularly, it relates to producing and digitizing a number of images to create a digital library of images, producing and providing a digital library of texts corresponding to the images in the library of images, providing an image from outside the digital library, digitizing it and comparing it to the digital images in the digital library, and selecting from the digital library of texts a text which corresponds to the outside image, and using the selected text to produce at least a portion of a record.

In many fields and technologies it is important to create and maintain a record, or history or narrative, of situations, facts, operations or procedures. Such records are important for achieving repeatability and accuracy, for educational or evaluative purposes, and/or for reconstructive purposes. For example, in industrial production, they may be used to detect deviations from specifications and production standards, and/or they may be used to create a "standard operating procedure" ("SOP"). In the legal field, transcripts or records of legal proceedings may be used to revisit or review the propriety of proceedings and decisions. In research or experimental science, laboratory notebooks or journals may reflect and/or evidence results of chemical combinations or hypothesis. In medicine, medical records and transcripts of surgical procedures may be used for diagnosis, to determine subsequent treatments, and/or to determine or assess prognoses. In each of these examples, and in many other instances and fields, records provide a database or library of knowledge, teach, instruct or inform about past practices or products, and/or aid in the detection and elimination of anomalies and inaccuracies.

Making and keeping a record has been, and is, a painstaking process. Typically, it has involved an individual hand writing a description or narrative, which may then be archived or preserved for reference by the individual who created it, or others. Developments in recording technologies, e.g., photography, sound and voice recording and storage, digital storage of information, etc., have somewhat eased the burden of creating a record, but there is room for further improvement.

Turning to the field of medicine, in which the present invention finds particular, but not exclusive, applicability, medical records were typically produced by the care giver writing by hand, for example, in a patient's chart. More recently, a care giver or physician may speak into a sound recording machine, or dictate, a description of a treatment or procedure. The recording or "tape" is then transcribed by others into a written record or chart. Also more recently, photographic records may be used. For example, a surgical procedure may be filmed, and the film may be accompanied by a verbal description dictated or spoken by the surgeon or attending physician while the procedure is taking place. Notwithstanding these advances, problems and inefficiencies remain.

One problem stems from outsourcing dictated medical records, even when such outsourcing is to organizations or people specializing in the transcription of medical records. The dictated item must be communicated to the transcriptionist, and back, and physicians and care givers must review and edit the transcription, leading to inefficiencies in time and handling, and increased costs. Another problem is the time interval or delay between the procedure and the availability of the transcript. This is true even when a physician dictates during a procedure, which itself may interfere with the concentration or performance of the physician. Typically, current medical record procedures still require a physician or surgeon to go to a workstation to dictate a description of a procedure or treatment after it is completed, at least to review a transcript, but in most instances, to dictate a description as well.

There are some attempts to improve the efficiency of producing medical records. For example, there are service providers, e.g., Speech Machines, Inc. and MedQuist, Inc., which specialize in transcribing dictated descriptions of medical treatments. They may use voice or term recognition systems (e.g., Dragon System's "Naturally Speaking," IBM's "ViaVoice" and Lernout & Hauspie's "VoiceXpress") wherein a vocal term or phrase is recognized by a computer which then converts it into a word-processing result. U.S. Pat. No. 6,031,526 discloses a system wherein generating electronic and printed medical records provides automatic integration of captured video still images and voice dictated information concerning the image, and wherein a voice recognition module allows the system to respond to voice commands and automatically transcribe the dictated text into a word processing document. Another, generally similar example of such systems is that provided by cMore Medical Solutions, Inc. of Minneapolis, Minn. Although efficiency of making a record may be increased, there are still transmission and handling delays, even when use is made of browser or internet-based systems.

One way to relieve physicians' dictation burden would be to film or photograph a treatment or surgical procedure and use the recorded images to trigger a descriptive text. Such a solution would likely involve a computer or computers. U.S. Pat. No. 4,996,707 (O'Malley et al.) discloses a computer system having the capability to receive and store graphic images which might be useful in such a solution. The system includes software that can digitize images, enabling them to be stored in memory and then accessed and used for various purposes, including identification, printing, or converting the digitized images to speech using a "text-to-speech" module. There is no disclosure or suggestion of digitizing a large number of images to create a digital library of images, providing an image from outside the digital library, digitizing it and comparing it to the digital images in the digital library, and providing for the production of a descriptive text associated with the image from outside the digital library.

Computers and storage and manipulation of data using computers hold promise for improving medical record creation, record keeping and use of stored medical records. For example, U.S. Pat. No. 5,050,220 involves an optical fingerprint correlator wherein a fingerprint is digitized, and then may be compared to a database of fingerprints to try to find a match. Such a correlator could be adapted to identify a patient, pull up the patient's medical record, and compare a current or recent diagnostic image (e.g., an MRI image) to the record. U.S. Pat. No. 5,031,228 discloses another image recognition system and method for identifying a pattern in images, and U.S. Pat. No. 5,668,897 discloses a method and apparatus for imaging and image processing, including digitizing an image and comparing the digitized image against a codebook of stored digital images. None of these patents discloses using an image to select or create a text describing an image.

The use of microprocessors, computers and computer management of data, including images, in the field of medicine is reflected in U.S. Pat. Nos. 5,241,472; 5,261,404; 5,740,802; 5,951,571; 5,961,456 and 6,024,695, the disclosures of which patents are incorporated herein by reference. Typically, the systems and methods disclosed in these patents involve obtaining images, digitizing the images and storing and/or manipulating or using the images, e.g., in U.S. Pat. No. 5,241,472 to create a text file. In U.S. Pat. No. 5,951,571 a computer is used to access a data storage unit containing previously acquired and digitally stored images of a patient. U.S. Pat. No. 5,961,456 is directed to a system and method for using current actual images and computer generated reference images, and the U.S. Pat. Nos. 5,261,404 and 6,024,695 use computer technologies to use images to position or guide surgical procedures. The U.S. Pat. No. 5,740,802 involves interactive computer generated models obtained from medical diagnostic imaging data to allow a surgeon to view internal and external patient structures and their relation to adjust the surgery accordingly. None of these patents discloses or suggests the use of the disclosed technologies to facilitate dictation, i.e., to help a physician create a medical record describing an administered treatment or procedure by using an image drawn from the treatment or procedure to trigger or select a text descriptive of the image, wherein the text then becomes at least part of a medical record.

U.S. Pat. Nos. 5,704,371 and 6,026,363 disclose a medical history documentation system and method which may involve a microprocessor to collect data and down load it to a computer which may store and process the data to provide a patient history text. There is no disclosure of using images to provoke the selection of a text corresponding to the image, wherein the selected text may become the record, or portion of the record, of a medical treatment or surgical procedure.

Notwithstanding the advances represented by the above mentioned technology and patents, it would be advantageous if there were a method and apparatus for more efficiently and accurately making a history or record, particularly, but not exclusively, a medical record.

SUMMARY

In one embodiment, the present invention provides methods and apparatus for making a history or record, particularly, but not exclusively, of a medical treatment or surgical procedure.

In one embodiment, the present invention relates to producing and digitizing a number of images to create a digital library of images, providing an image from outside the digital library, digitizing it and comparing it to the digital images in the digital library, and producing a text associated with the image from outside the digital library.

In one embodiment, the present invention comprises a visual input device, a processor, a visual output device, and a transmission system linking the input device, the processor and the output device.

In one embodiment, the present invention relates to the capture, recognition and manipulation of data.

In one embodiment, the present invention relates to the capture, recognition and manipulation of data, particularly data concerning medical treatment, wherein the treatment may be broken down into a series of steps, and wherein each step may be described by standard language understood by one skilled in the art. This feature of the present invention is well-suited to use in surgical procedures, wherein any one procedure may be accomplished in one of usually several or so standard or routine ways, wherein any one procedure may be broken down into steps or milestones, and wherein any one procedure usually involves encountering the same or similar physical structures.

An advantage of the present invention is that it facilitates creating a record, particularly, but not exclusively, a medical record.

In one embodiment, the present invention relates to producing and digitizing a number of images, related to a medical treatment, particularly a surgical procedure, to create a digital library of images, providing an image from outside the digital library, digitizing it and comparing it to the digital images in the digital library, and producing a text associated with the image from outside the digital library. In some embodiments, an image of an unusual, atypical and/or anomalous medical condition or situation may provoke, trigger or provide a "blank" text to be filled in later by the treating person. An advantage is better coordination of procedures and respective outcomes, as well as improving the time it takes for comparative or analytical information to become available. In some embodiments, the image from outside the digital library may be a real time image.

A feature of the present invention is image recognition, wherein a collection of images is available, each having an associated descriptive text, and wherein an image not in the collection is compared to images in the collection to find a comparable or matching image, and associated text. The collection of images may be created by accumulating images originally not in the collection.

Another feature of the present invention is providing a library of descriptions or texts, each associated, related to and/or describing a structure, step or quality depicted or captured as an image. In some embodiments, the structure, step or quality is an aspect of a medical treatment or surgical procedure.

Another feature of the present invention is providing coordination of procedures and outcomes, e.g., the outcome of a medical treatment may be compared to outcomes of similar procedures, anomalies or abnormalities may be compared and/or identified, a record of a procedure may be available for consideration more quickly, etc.

In one embodiment of the method and apparatus of the present invention, a live or real-time image obtained during a surgical procedure is compared to stored images of previous surgical procedures to find a stored image similar or substantially identical to the live image, whereupon a script or text describing the live image is produced.

In some embodiments, the method of the present invention involves creating a collection or library of images drawn from surgical procedures, e.g., laparoscopic gallbladder procedures, cholecystectomy, hernia procedures, etc., wherein the individual images comprise pictorial representations of anatomy or structures encountered and steps undertaken during the procedures. In some embodiments, the collection of images may be sorted or indexed into sets or groups, wherein a set or group may be comprised of any number of generally similar images depicting a step or action which is typically common to a selected procedure, e.g., a step in a laparoscopic gallbladder procedure.

In one embodiment, the present invention encompasses breaking a surgical procedure into a series of steps, capturing or representing each step in an image, each image depicting the step and structures and qualities associated with the step, digitizing the images, and creating a text respectively descriptive of a step and images of that step, wherein the text comprises standard language understood by one skilled in the art, and may be selected, without substantial change, to describe the similar step of another generally similar surgical procedure, the text selection being accomplished on the basis of comparing images from the generally similar surgical procedure to the previously acquired images.

In one embodiment, the present invention relates to producing a number of digital images to create a digital library of images, providing an image from outside the digital library, digitizing it (if it is not already digital) and comparing it to the digital images in the digital library, and producing a text associated with the image from outside the digital library, wherein the digital images and text may be considered data and may be analyzed and/or manipulated to provide likely or actual: diagnostic outcome information; a classification or sort of procedures by type; possible therapeutic, corrective or repair steps; and a recommendation of optional, and/or the optimal, therapeutic, corrective or repair steps. In one embodiment, the present invention may provide for statistical analysis of subject procedures and outcomes, for example, surgical procedures, whereby the optimum or best step or action within a given procedure may be identified.

In one embodiment of the present invention, data may be accumulated, analyzed and reported.

In one embodiment, the present invention relates to methods and apparatus for viewing and taking an image or picture of a number of objects or situations, processing the images, including digitizing and storing them and creating a text describing each of them, viewing and taking another image or picture, processing the another image, including digitizing and storing it, and selecting one of the texts which corresponds to the another image.

An advantage of the present invention is the creation and use of a world-wide network of procedural information, including, but not limited to medical and/or surgical information, wherein the information may be accessed by those engaged in similar procedures and/or wherein the information may evolve, e.g., the data comprising the information may increase, both in number and sophistication.

Another advantage of the methods and apparatus of the present invention is that they may be used to create an "early warning" system wherein a real-time image is compared to a library of images which includes images of anomalous, abnormal and/or dangerous structures, situations and/or qualities and, if a similarity is detected, a warning or alert is provided. In one embodiment, the present invention takes advantage of the routine, repetitive or common steps typical of a given procedure, for example, a surgical procedure, to provide for the early warning system, and/or to provide for a predictive and/or educational system, wherein a accessible and/or searchable database comprising a collection of images and texts to provided for consideration before undertaking a procedure.

Other features and advantages of methods and apparatus of the present invention will become more fully apparent and understood with reference to the accompanying description, drawings and claims.

BRIEF DESCRIPTION OF THE DRAWINGS

This patent and/or patent application file contains photographs executed in color. Copies of this patent or patent application publication with color photographs will be provided by the Office upon request and payment of the necessary fee.

FIG. 1 comprises representative images exemplifying images for use in embodiments of the present invention.

FIG. 2 comprises representative images exemplifying images for use in embodiments of the present invention.

FIG. 3 comprises representative images exemplifying images for use in embodiments of the present invention.

FIG. 4 comprises representative images exemplifying images for use in embodiments of the present invention.

FIG. 5 comprises representative images exemplifying images for use in embodiments of the present invention.

FIG. 6 comprises representative images exemplifying images for use in embodiments of the present invention.

FIG. 7 comprises representative images exemplifying images for use in embodiments of the present invention.

FIG. 8 comprises representative images exemplifying images for use in embodiments of the present invention.

FIG. 9 comprises representative images exemplifying images for use in embodiments of the present invention.

FIG. 10 comprises representative images exemplifying images for use in embodiments of the present invention.

FIG. 11 comprises representative images exemplifying images for use in embodiments of the present invention.

FIG. 12 comprises representative images exemplifying images for use in embodiments of the present invention.

FIG. 13 comprises representative images exemplifying images for use in embodiments of the present invention.

FIG. 16 depicts another embodiment of the present invention

FIG. 17 depicts another embodiment of the present invention

DETAILED DESCRIPTION

Figure 14:
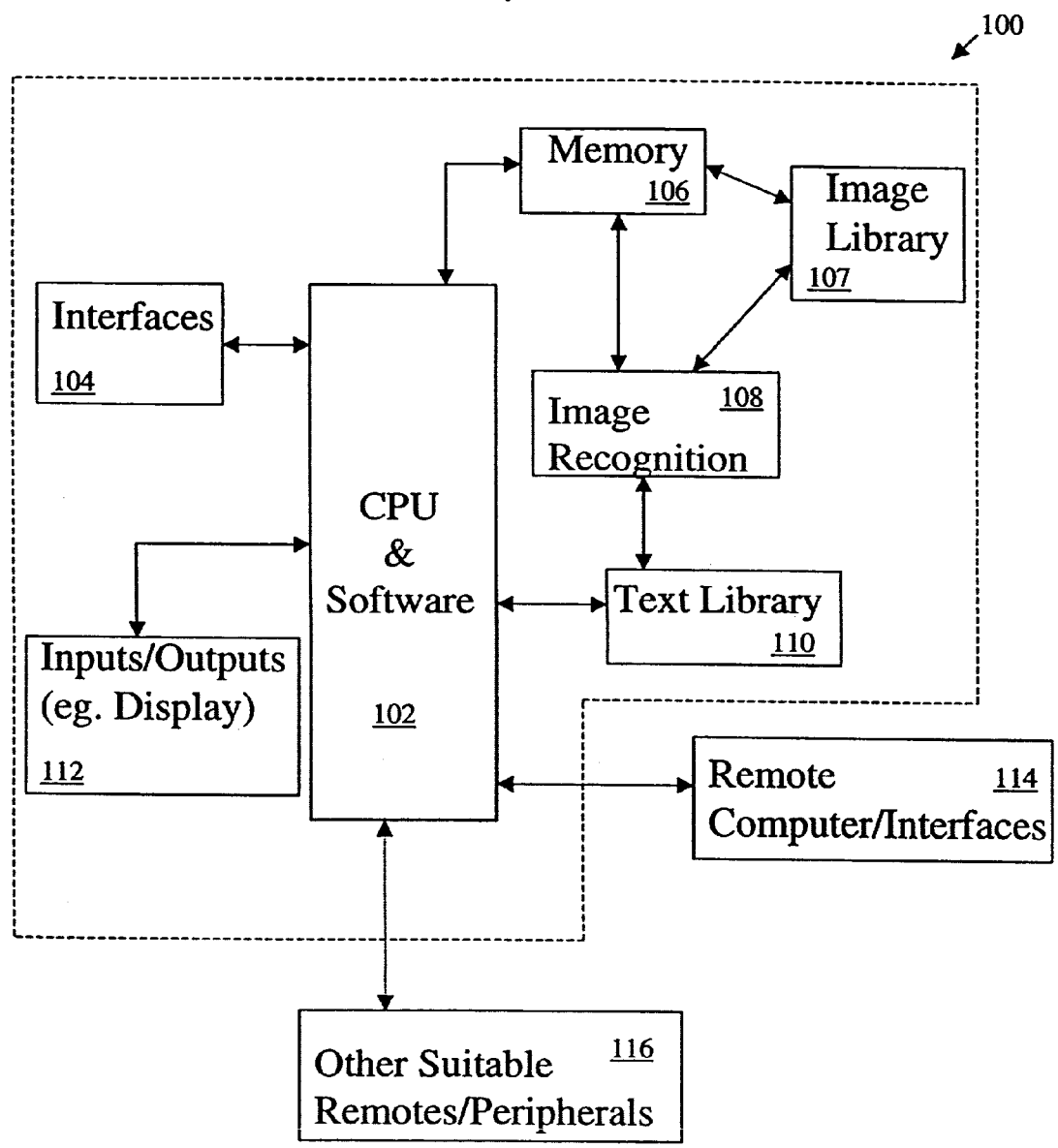
FIG. 14 depicts one embodiment of a computer or processing system of the present invention.

The accompanying figures and this description depict and describe embodiments of a process or method and apparatus in accordance with the present invention, and features, steps and components thereof. As used herein, the terms "medical treatment", "surgery" and "surgical procedure" are intended to encompass any medical care giver/patient interaction, including, but not limited to office examinations, surgical procedures, physical therapy, administration of medication, consults, diagnostic procedures, etc. In some embodiments, the methods and apparatus of the present invention may comprise integrated structures or features, such as a network of microprocessors, communication links and the like, at various locations, including a central station, and the steps may be performed at various locations. Although electronic, e.g., digital, apparatus and methods are contemplated, the present invention is also intended to encompass "hard copy," e.g., video images, photographs, printed documents, including directories or indices, and the like.

Unless specifically disclosed or taught, any suitable electronic devices and coupling or linking methods and apparatus may be used in the present invention, for example, the present invention may incorporate appropriate microprocessors, integrated circuits, chips, memory structures, wireless links, internet links, telephony, optical fiber technology, data storage technology, etc.

Any references to positional and/or temporal locations, e.g., the location of microprocessors and/or the order of processing or steps, are intended for convenience of description, not to limit the present invention to any one positional or temporal orientation.

Although the microprocessor or controller, or microprocessors, for the present invention can be any controller or microprocessor-based system, and more than one may be involved, in one embodiment of the invention, the controller comprises a suitable central processing unit and suitable peripheral devices. In one embodiment, a suitable peripheral device may be a field programmable microcontroller peripheral device that includes, like the processing unit, programmable logic devices, EPROMs, and input-output ports. Typically, instructions are stored in the controller as program logic, which might be found as RAM or ROM hardware in the processing unit or peripheral device. (Since the processing unit may have some memory capacity, it is possible that some of the instructions are stored in the processing unit.) As one skilled in the art will recognize, various implementations of program logic are possible. The program logic could be either hardware, software, or a combination of both. Hardware implementations might involve hardwired controller logic or instructions stored in a ROM or RAM device. Software implementations would involve instructions stored on a magnetic, optical, or other media that can be accessed by the processing unit. Communication implementations may be wired, optical or wireless.

FIG. 14 depicts one embodiment of the processing system of the present invention where an apparatus 100 is used to process the images received from inputs 112 and generate text output also depicted at block 112 and which may be stored in a text library. A central processing unit or CPU 102 utilizes appropriate software to operate the system. The image library 107 contains the images and is stored in the memory 106. The image recognition device 108 compares a newly acquired image to the images in the library. Once the image is recognized the computer will select the text corresponding to the recognized image. The apparatus 100 can be connected to appropriate interfaces 104 and/or to a remote computer or interface 114 and/or other suitable remotes or peripherals 116.

The following examples reflect one embodiment of the present invention wherein at least a portion of a dictation record regarding a surgical procedure corresponds to an image captured during that procedure and during other similar procedures. In other words, each of the following examples of dictation records concerning actual surgical procedures includes certain steps or elements in common, and those elements or steps, and the entire procedure, may be photographed during the procedures of the examples. The examples are generally typical of such procedures and, thus, the pictures of common elements or steps will be generally typical. The pictures may be digitized using a suitable method, and stored in a digital library. Pictures taken during another (e.g., real time) procedure, not one of the examples, but another similar procedure, may be digitized and compared to the pictures in the digital library. Because the another procedure is similar to the procedures already represented in the digital library, pictures of steps from it will correspond or match closely pictures of steps from the previous similar procedures. The corresponding or matching picture(s) in the digital library may be used to trigger a text descriptive of the picture(s) which will also be descriptive of the step of the another (or real time) procedure.

FIGS. 1-13, including FIGS. 1a-1e, 2a-2c, 3a-3d, 4a-4i, 5a-5f, 6a-6c, 7a-7g, and 8a-8b, 9a-9c, 10a-10i, 11a-11e, 12a-12e, and 13a-13j, are actual images taken from the procedures of the following Examples 1-6 (gallbladder) and Examples 1-4 (hernia) or from generally similar procedures. Any surgical procedure, including those of the examples, may be imagined as a film or movie, i.e., a continuous series of images, and FIGS. 1-13 comprise selected stills or individual images clipped or selected from the film. Images identified as Figures corresponding to the steps of the procedures of Examples 1-6 (gallbladder) and Examples 1-4 (hernia) have been referenced in the dictation text of those examples. It should be appreciated that other and/or additional common, routine and/or similar steps, dictation portions and images may be identified. In the following examples, grammatical and typographical errors from the original transcribed dictation record have been corrected.

The following six examples are actual dictated records of gallbladder procedures. It should be understood that an advantage of the present invention derives from the fact that surgical procedures are repetitive in terms of what is seen, and the words used to describe what is seen. Indeed, routinization in procedures is important to surgeons and patients because anatomy usually conforms from patient to patient. Although a surgeon may slightly vary steps and/or the order of steps in a procedure, and although there may be some slight variations in the angle of vision, color, etc., there will be steps and images which are substantially similar from procedure to procedure. Again, the parenthetical reference to a figure or figures following each step is to link the step with various corresponding sample figures and are outlined by bold lettering.

EXAMPLE 1

Gallbladder

Operative Procedure: Laparoscopic Cholecystectomy, Cholangiography.

Description of Procedure:
  Introduction
    After satisfactory endotracheal anesthesia was obtained the patient's abdomen was prepped and draped in the usual fashion. A CO2 pneumoperitoneum was instilled through a 10 mm trocar placed cephalad to the umbilicus at 4 liters per minute of flow pressure equal to or less than 17 mmHg to a total of 4.5 liters. A 45° angle laparoscope was introduced. Examination of the abdomen was unremarkable except for the gallbladder which showed multiple adhesions. These were of a chronic type. Under direct vision a 5 mm trocar was placed along the right anterior axillary line.
    Step 1: Fundus of the gallbladder was grasped. (FIG. 1, 1a-1e)
    Step 2: A # 17 gauge pericardial needle was passed percutaneously into the gallbladder. Then 30 cc of bile was aspirated and replaced with 60 cc of 50 percent Hypaque and two separate aliquots of 50 and 10 cc each with x-rays taken at the conclusion of infusion of each aliquot. After x-rays were taken and examined excess Hypaque was aspirated and the needle removed under direct vision. (FIG. 2, 2a-2c)
    Step 3: Two 5 mm and a 12 mm trocars were placed in the right mid abdomen. The patient was placed in reversed Trendelenburg's position. (FIG. 3, 3a-3d)
    Step 4: The neck of the gallbladder was grasped and dissected out from surrounding tissue. The junction of the cystic duct, common duct, and common hepatic duct was visualized. (FIG. 4, 4a-4i)

Step 5: The cystic duct was dissected free, clipped proximally and distally, divided. (FIG. 5, 5a-5f)
Step 6: The cystic artery was electrocoagulated with bipolar cautery. (FIG. 6, 6a-6c)
Step 7: The gallbladder was removed off the liver bed with bipolar cautery in retrograde fashion. (FIG. 7, 7a-7g)
Step 8: The gallbladder was led out of the abdomen through the 12 mm trocar. (FIG. 8, 8a-8b)

Conclusion

The abdomen was irrigated with saline and the irrigant suctioned out. Trocars were removed. The deep tissue was closed with interrupted #2 Vicryl to the fascia, continuous running #4 Vicryl subcuticular to reapproximate the skin. Closure was reinforced with Steri-Strips. Gauze bandage and paper tape with dressings were applied. Blood loss was negligible. She left the Operating Room in satisfactory condition. (End of Example 1)

EXAMPLE 2

Gallbladder

Operative Procedure:
1. Laparoscopic cholecystectomy with cholecyst cholangiography.
2. Excision of chronic infected, nonhealing cyst of the back with conversion from transverse to oblique orientation using Z-plasty technique.

Description of Procedure:
Introduction
After satisfactory endotracheal anesthesia was obtained, the patient's abdomen was prepped and draped in the usual fashion, after which CO2 pneumoperitoneum instilled through a 10 mm Innerdyne trocar placed cephalad to the umbilicus and 4 L/min flow, pressures equal to or less than 17 mm Hg to a total of 5 L. A 45-degree angle laparoscope introduced. Thorough examination of the abdomen revealed a right inguinal hernia. Otherwise, there were a few adhesions to the gallbladder, a few stones in the gallbladder of cholesterol origin, and at the time of cholangiography, one was able to see a normal anatomical pattern. No defects in the common duct with dye entering freely into the duodenum. Under direct vision, a 5 mm trocar placed along the right anterior axillary line.
Step 1: Bi-toothed biopsy forceps used to grab the fundus of the gallbladder for upward retraction. (FIG. 1, 1a-1e)
Step 2: A 17 gauge pericardial needle passed percutaneously into the gallbladder, excess bile aspirated, replaced with 60 cc of 50% Hypaque, delivered in two aliquots of 50 and 10 cc each. At the end of infusion of each aliquot, x-rays were taken. These were examined. Findings as listed above. Excess dye was then aspirated, the needle removed. (FIG. 2, 2a-2c)
Step 3: Additional 5 mm and 12 mm trocar placed in the right mid abdomen. Patient placed in reversed Trendelenburg position. (FIG. 3, 3a-3d)
Step 4: The neck of the gallbladder was elevated, the cystic duct dissected from the gallbladder to junction with the common bile duct, cystic artery identified along with the lymph node of Calot. (FIG. 4, 4a-4i)
Step 5: The cystic duct was clipped×3 proximally, distally, the cystic duct divided. (FIG. 5, 5a-5f)
Step 7: The gallbladder dissected off the liver bed with bipolar cautery. (FIG. 7, 7a-7g)
Step 6: The cystic artery was electrocoagulated with bipolar cautery. (FIG. 6, 6a-6c)
Step 8: The gallbladder was then delivered out of the abdomen through the leading edge of the 12 mm trocar. (FIG. 8, 8a-8b)

Conclusion

The stones were removed before the entire gallbladder could be removed from the abdominal cavity. Once done, the 12 mm trocar was replaced, the right upper quadrant irrigated with saline until clear. No bile or blood was noted. Irrigant suctioned out along the right lateral sulcus of the liver. Instruments removed, CO2 let out through open valves and external massage. Trocars removed, deep tissue closed with 2-0 Vicryl, skin with continuous running 4-0 Vicryl and ½ inch Steri-Strips. Tegaderm dressings applied. Tolerated well. At that point, we placed the patient prone. The lesion in the upper mid back measured approximately ¾ to 1 inch in transverse diameter. The cyst was partially filled with material. It was opened and chronically fistulized to the skin. Actually, the cyst traveled cephalad a fair distance underneath the skin. The area was locally infiltrated with 0.25% Marcaine with epinephrine as were the previous sites of the gallbladder trocars. A Z-plasty was marked on the skin. The mass itself was first excised. Z-plasty flaps were dissected out. Bleeding controlled with electrocoagulation. After the flaps were completed, they were placed in the proper orientation, allowing a central vertical incision and two adjacent oblique incisions. The closure was completed with interrupted 4-0 Vicryl to the subcutaneous tissue. It should be mentioned a #7 round Jackson-Pratt drain was placed into the depths of the incision, brought out through a lateral stab wound, tied to the skin with 2-0 silk. After stabilization of the flaps, the skin was reapproximated with continuous running 5-0 Vicryl. Sterile compressive dressing applied. Tolerated well. Blood loss negligible. Left the operating room now in satisfactory condition. (End of Example 2)

EXAMPLE 3

Gallbladder

Operative Procedure: Laparoscopic Cholecystectomy with Cholecyst Cholangiography.

Description of Procedure:
Introduction
After satisfactory endotracheal anesthesia was obtained, the patient's abdomen was prepped and draped in the usual fashion after which CO2 pneumoperitoneum instilled with a Veress needle placed cephalad to the umbilicus at 2.5 L full to pressures equal to or less than 16 mmHg to a total of 6 L. The Veress needle then removed and replaced with a 10-mm InnerDyne trocar. A 45-degree-angle laparoscope introduced. General examination of the abdomen. Findings as listed above. No adhesions were present to the gallbladder. The gallbladder appeared gray in color. Under direct vision, a 5-mm trocar was placed along the right anterior axillary line.
Step 1: The bitoothed biopsy forceps were used to grab the fundus of the gallbladder with upward retraction. (FIG. 1, 1a-1e)
Step 2: A 17-gauge pericardial needle passed percutaneously into the gallbladder. Approximately 30 cc of dark brown bile was aspirated and 60 cc of 50%

Hypaque instilled in two separate aliquots of 50 and 10 cc each. At the end of the infusion of each of the two aliquots, x-rays were taken and examined in the operating room, with the findings as listed above. The excess Hypaque was then aspirated, the needle removed. (FIG. 2, 2a-2c)

Step 3: Under direct vision a 5-mm and 12-mm trocar were placed in the right midabdomen. (FIG. 3, 3a-3d)

Step 4: Bitooth biopsy forceps used to place the neck of the gallbladder on stretch after placing the patient in reverse Trendelenburg position. Everest Medical bipolar curved scissors and forceps used to uncover the cystic duct and the cystic artery. The cystic duct was followed to its junction with the common bile duct. (FIG. 4, 4a-4i)

Step 5: The cystic duct was clipped times 2 proximally and once distally, divided. (FIG. 5, 5a-5f)

Step 6: The cystic artery electrocoagulated with bipolar cautery. (FIG. 6, 6a-6c)

Step 7: Gallbladder dissected off the liver bed with bipolar cautery aided by bipolar scissors dissection. (FIG. 7, 7a-7g)

Step 8: After removal of the gallbladder from the liver, the gallbladder fossa was examined for bile or blood. There was none. The gallbladder then placed into a bag which was then brought out half way through the abdomen and ring forceps used to extract whatever was left of the gallbladder itself and the bag as well. (FIG. 8, 8a-8b)

Conclusion

With all of this removed, the 12-mm trocar was placed back into the abdomen, the right upper quadrant irrigated with saline until clear, and the instruments then removed. CO2 let out through external massage. The trocars were removed. The deep tissue was closed with 2-0 Vicryl, the skin with continuous running 4-0 Vicryl, with ½ inch Steri-Strips. Each puncture site was locally infiltrated with 0.25% Marcaine with epinephrine for postoperative pain relief. A Tagaderm dressing was applied. Tolerated well. Blood loss negligible. (End of Example 3)

EXAMPLE 4

Gallbladder

Operative Procedure; Laparoscopic Cholecystectomy

Description of Procedure:
Introduction
After satisfactory endotracheal anesthesia was obtained, the patient's abdomen was prepped and draped in the usual fashion, after which CO2 pneumoperitoneum was instilled through a 10-mm InnerDyne trocar placed cephalad to the umbilicus at 4 L per minute flow pressures equal to or less than 16 mmHg to a total of 5 L. A 45-degree-angle laparoscope was introduced. Sterile examination of the abdomen and findings as listed above.

Step 3: Under direct vision, 5-mm trocars times two were placed in the right midabdomen along with the 12-mm InnerDyne trocar. (FIG. 3, 3a-3d) Multiple adhesions were present on the gallbladder. These were taken down with bipolar cautery. The gallbladder was then elevated out of the wound after being freed of adhesions.

Step 4: Careful dissection of the gallbladder as it narrowed down into the cystic duct was noted. Medial dissection was unremarkable. (FIG. 4, 4a-4i)

Step 5: Once the dissection was completed, the clips were placed proximally on the cystic duct times three, one distally, the cystic duct divided. (FIG. 5, 5a-5f) Then dissected off in a retrograde fashion using bipolar cautery. The gallbladder represented an intrahepatic gallbladder as well as subacute. The dissection went very smoothly without any bleeding.

Step 6: The cystic artery had been identified and electrocoagulated. (FIG. 6, 6a-6c)

Step 7: We located the anterior cystic artery. The dissection continued smoothly off the liver bed. (FIG. 7, 7a-7g)

The liver bed was then inspected for any residual bleeding or bile staining and none was evident except some bleeding, a very minimal amount, toward the bottom of the liver bed, and a piece of Surgicel was placed here for control. This was then reexamined after total removal of the gallbladder and again no blood or bile was now present.

Step 8: The gallbladder after being removed was then led partially out of the abdomen through the 12-mm trocar and grabbed with clamps, incised, the bile suctioned out, and small stones were then removed with a ring forceps until the gallbladder was small enough in size to pop through the opening. (FIG. 8, 8a-8b)

Conclusion

The trocar was then replaced, the right upper quadrant irrigated with saline, some irrigant suctioned off, and the procedure terminated with removal of instruments. Open valves on the trocars. External massage to remove CO2 gas. The trocars were removed and the tissue closed with interrupted 2-0 Vicryl sutures, the skin with continuous running 4-0 Vicryl and ½-inch Steri-Strips. Tegaderm dressing was applied. Tolerated well. Left the operating room in satisfactory condition. (End of Example 4)

EXAMPLE 5

Gallbladder

Operative Procedure: Laparoscopic Cholecystectomy and Cholecyst-Cholangiography.

Description of Procedure:
Introduction
After satisfactory endotracheal inhalation anesthesia was obtained, the patient's abdomen was prepped and draped in the usual fashion, after which CO2 pneumoperitoneum was instilled through a 10 mm Innerdyne trocar placed cephalad to the umbilicus at a 4 L/min flow with pressures equal to or less than 17 mmHg to a total of five liters. A 45 degree angle laparoscope was introduced into the abdomen and general examination of the abdomen unremarkable except for findings as listed above. Under direct vision, a 5 mm trocar was placed along the right anterior axillary line.

Step 1: Bi-toothed biopsy forceps grasped the fundus of the gallbladder with upward retraction. (FIG. 1, 1a-1e)

Step 2: A 17 gauge pericardial needle was passed percutaneously into the gallbladder, excess bile aspirated and 60 cc of 50% Hypaque introduced in 50 and 10 cc aliquots. At the end of each aliquot x-rays were taken and cystic duct obstruction was noted. Excess dye was then removed, the needle removed. (FIG. 2, 2a-2c)

Step 3: A 5 mm and 12 mm trocars placed in the right mid abdomen under direct vision. The patient was placed in reverse Trendelenburg position. (FIG. 3, 3a-3d)

Step 4: The gallbladder was then grabbed just above the stone which was impacted in the neck. The cystic duct was fully dissected away from the gallbladder and the anterior and posterior cystic artery noted. (FIG. 4, 4a-4i)

Step 5: After all three structures were identified clearly, they were clipped, appropriately divided. (FIG. 5, 5a-5f)

Step 7: The gallbladder then dissected off the liver bed with bipolar cautery and scissors. (FIG. 7, 7a-7g)

Step 8: It was then put into an extraction bag, brought halfway out of the abdomen through the 12 mm trocar and piecemeal we were able to remove the gallbladder bag intact. (FIG. 8, 8a-8b)

Conclusion

The puncture site was irrigated with saline. The abdomen was copiously irrigated until clear. No drains were placed. The trocars were removed, the deep tissue closed with interrupted 2-0 Vicryl and the skin with continuous running 4-0 Vicryl subcuticular. Half inch Steri-Strips were applied, Tegaderm dressings applied, the wounds locally infiltrated with 0.25% Marcaine with epinephrine for postoperative pain relief and the procedure terminated. The patient tolerated it well and left the operating room in satisfactory condition. (End of Example 5)

EXAMPLE 6

Gallbladder

Operative Procedure: Laparoscopic Cholecystectomy, Cholangiography.

Description of Procedure:
Introduction
After a satisfactory endotracheal anesthesia was obtained the abdomen was prepped and draped in the usual fashion. A CO2 pneumoperitoneum was instilled through a 10 mm InnerDyne trocar placed cephalad to the umbilicus at four liters per minute flow. Flow pressures were equal to or less than 17 mmHg to a total of five liters. The 45° angle laparoscope was introduced. General examination of the abdomen showed findings as described above.

Step 3: Under direct vision a 5 mm and 12 mm disposable trocar was placed in the right upper quadrant along with a third trocar, 5 mm. (FIG. 3, 3a-3d)

Step 1: Bitooth biopsy forceps were used to grasp the fundus of the gallbladder. (FIG. 1, 1a-1e)

Step 2: A #17 gauge pericardial needle was passed percutaneously into the gallbladder and 30 cc of dark bile was aspirated. Then 60 of 50% Hypaque was instilled through separate aliquots, and 50 and 10 cc each. X-rays were taken at the conclusion of each aliquot infusion. Findings are as noted above. Excess Hypaque was aspirated and the needle removed. The patient was placed in reversed Trendelenburg position. (FIG. 2, 2a-2c)

Step 4: The gallbladder was grasped at the neck. Moderate amount of inflammation was noted in the wall with edema. The lymph node of Calot was identified and stripped off the gallbladder. The gallbladder junction with the cystic duct was identified which was then traced down to the common bile duct. The cystic artery was identified and all these structures lay in normal anatomic position. The cystic duct was dissected free of surrounding tissue. (FIG. 4, 4a-4i)

Step 5: Two clips were then placed proximally and two distally. The duct was divided. (FIG. 5, 5a-5f)

Step 6: The cystic artery was electrocoagulated with bipolar cautery and divided. FIG. 6, 6a-6c)

Step 7: The gallbladder was then dissected off the liver bed with bipolar cautery in a retrograde fashion until it was free from the liver. (FIG. 7, 7a-7g)

Step 8: It was then brought partially out of the abdomen through the 12 mm trocar. (FIG. 8, 8a-8b)

Conclusion

The instrument was then placed within the gallbladder to crush the stone into multiple small pieces which were then removed piecemeal until the gallbladder popped through the hole. Some fragments got loose but were retrieved both intra-abdominal with a pelviscopic scoop and within the wound itself while pulling the gallbladder through the wound with pickups. The whole tract was irrigated copiously with saline until all fragments were cleaned up. The inside of the abdomen was irrigated with saline, especially the gallbladder fossa and along the right lateral sulcus of the liver, all of which was aspirated. No evidence of any bleeding, bile leakage was noted. Instruments were removed. Trocars were removed after expelling co2 gas with external massage. After removal of the trocars the deeper tissue was reapproximated with #2-0 Vicryl and skin with continuous running #4 Vicryl. Half-inch Steri-Strips were placed. Tegaderm dressing was applied. The patient tolerated the procedure well. Blood loss was negligible. No complications were apparent. (End of Example 6)

The present invention can be used for various types of procedures in addition to the prior 6 examples just discussed. Another example is for use in hernia procedures. The following four examples are dictation records from left inguinal hernia repair procedures. References have been inserted in each example to refer to FIG. 1 and FIGS. 9-13, including FIGS. 1a-1e, 9a-9c, 10a-10i, 11a-11e, 12a-12e, 13a-13j which comprise images actually captured during the procedure of Example 1-4 (hernia).

EXAMPLE 1

Hernia

Operative Procedure: Laparoscopic Repair of Left Inguinal Hernia with Polypropylene Mesh Description of Procedure:
Introduction
After satisfactory endotracheal anesthesia was obtained, patient's abdomen was prepped and draped in the usual fashion after which CO2 peritoneum instilled through a 10 mm trocar placed cephalad to the umbilicus at 4 liters/minute flow of pressures equal to or less than 16 mmHg to a total of 5 liters. The 45 degree angle laparoscope introduced. General examination of the abdomen with findings as listed above.

Step 1: Under direct vision, a 5 mm and 12 mm trocar placed in right and left mid abdomen respectively. (FIG. 1, 1a-1e)

Step 2: Patient placed in Trendelenburg position. Everest medical curved scissors and bitooth biopsy forceps used to develop a left curvilinear peritoneal flap directed posteriorly which allowed entry into the preperitoneal space. (FIG. 9, 9a-9c)

Step 3: Dissection of the space curved from the line of Douglas above to Cooper's ligament below beyond the midline and lateral to the internal ring. (FIG. 10, 10a-10i)

Step 4: Direct space hernia was evident. A very small amount of fat was contained within the internal ring which was essentially normal in size and this was not reduced. A piece of polypropylene mesh measuring 6×5 inches was tightly rolled up into 10/11 mm trocar, placed on the 12 mm trocar and popped into the preperitoneal space on the left. This was unfurled, covered with the inguinal femoral area. (FIG. 11, 11a-11e)

Step 5: Stapled in place. (FIG. 12, 12a-12e)

Step 6: Pressure was then reduced to 5-6 mmHg, the leaves of peritoneum then reapproximated with closely placed staples. (FIG. 13, 13a-13j)

Conclusion

When complete, instruments were removed, CO2 let out through open valves and external massage. Trocar was removed, deep tissue closed with interrupted 2-0 Vicryl, skin with continuous running 4-0 Vicryl, Steri-Strips applied, Tegaderm placed. Tolerated well. Blood loss negligible. Left the operating room in satisfactory condition. (End of Example 1)

EXAMPLE 2

Hernia

Operative Procedure: Laparoscopic Repair of Recurrent Left Inguinal Hernia with Polypropylene Mesh Description of Procedure:

Introduction

After satisfactory general endotracheal anesthesia was obtained, the patient's abdomen was prepped and draped in the usual fashion after which CO2 pneumoperitoneum was instilled through a 10 mm Interdyne trocar placed cephalad to the umbilicus, 4 liters/minute flow and pressures equal to or less than 16 mmHg to a total of 4 liters. A 25 degree angle laparoscope was introduced and examination of the abdomen was unremarkable. A left inguinal hernia was noted. There is minimal weakness on the right and no additional surgery was done for that.

Step 1: Under direct vision, a 5 mm and 12 mm trocars were placed in right and left midabdomen, respectively. (FIG. 1, 1a-1e)

Step 2: The patient was placed in Trendelenburg position and a bitooth biopsy forceps and Everest Medical curved forceps and scissors used to develop a left curvilinear peritoneal flap directed posteriorly allowing entry into the preperitoneal space. (FIG. 9, 9a-9c)

Step 3: The space was dissected completely beyond the midline to the line of Douglas above to Cooper's ligament below. (FIG. 10, 10a-10i)

The hernia could be seen in the direct space constituting herniated fat, which was then reduced out of the hole, which could clearly be seen. The dissection carried well beyond the internal ring. A search for lipoma was negative. With the flap nicely developed.

Step 4: A piece of polypropylene mesh measuring 15×11.5 cm was placed into the preperitoneal space and used to cover the inguinal femoral area. (FIG. 11, 11a-11e)

Step 5: Staples were placed at all but the volar inferior portion mesh because of underlying nerve tissue in this region. (FIG. 12, 12a-12e)

Step 6: Pressure then reduced to 8 mmHg and leaves of peritoneum reapproximated with closely placed staples. (FIG. 13, 13a-13j)

Conclusion

Instruments were removed and CO2 removed through open valves. Trocars were removed. Deep tissue was closed with interrupted #2-0 Vicryl and skin with running #4-0 Vicryl and ½ inch Steri-Strips. Tegaderm dressings applied. Marcaine 0.25% with epinephrine was instilled in puncture sites for postoperative pain relief. Blood loss was minimal. The patient tolerated the procedure well and left the operating room in satisfactory condition. (End of Example 2)

EXAMPLE 3

Hernia

Operative Procedure: Laparoscopic Repair of Left Direct Space Weakness with Excision of Left Inguinal Lipoma Using Polypropylene Mesh.

Description of Procedure:

Introduction

After satisfactory endotracheal anesthesia was obtained, the patient's abdomen was prepped and draped in the usual fashion after which CO2 pneumoperitoneum was instilled through a 10-mm InnerDyne trocar placed cephalad to the umbilicus at 4 L per minute flow pressures equal to less than 16 mmHg. A 45-degree angle laparoscope introduced into the abdomen. The left inguinal hernia and weakness were noted, primarily over the direct space. The right inguinal area was unremarkable.

Step 1: Under direct vision, a 5-mm and 12-mm trocar was placed in the right and left midabdomen respectively. (FIG. 1, 1a-1e)

Step 2: The patient placed in Trendelenburg position and a 45-degree-angle laparoscope introduced. General examination of the abdomen as noted above. Using a bitooth biopsy forceps, the Everett Medical curved scissors and Kleptinger bipolar cautery, a left curvilinear peritoneal flap was directed posteriorly. (FIG. 9, 9a-9c)

Step 3: The preperitoneal space dissected thoroughly from beyond the midline to below. (FIG. 10, 10a-10i)

An extremely weak posterior space was noted. A lipoma of the cord was noted. In addition, there were multiple and enlarged lymph nodes present at the mouth of the slightly dilated internal ring. This site is considered to be unusual and is not customarily found, although such nodes are found in the region of the femoral ring. For that reason, a biopsy was taken of one of these nodes and sent for pathologic examination.

Step 4: After thorough dissection of the preperitoneal space, polypropylene mesh measuring 15×11.5 was rolled up in a 10-11 trocar placed down a 12-mm trocar and placed into the preperitoneal space. This was unfurled over the inguinal femoral area. (FIG. 11, 11a-11e)

Step 5: Held in place with staples. (FIG. 12, 12a-12e)

Step 6: The pressure was then reduced to 8 mmHg and the leaves of peritoneum reapproximated with closely placed staples. (FIG. 13, 13a-13j)

Conclusion

The instruments were removed and CO2 let out through open valves and external massage. The trocar was removed. The deep tissue was closed with interrupted 2-0 Vicryl, the skin with continuous running 4-0 Vicryl, with ½ inch Steri-Strips. A Tegaderm dressing was applied. Tolerated well. Blood loss negligible. Left the operating room in satisfactory condition. (End of Example 3)

EXAMPLE 4

Hernia

Operative Procedure: Laparoscopic Repair of Indirect Right Inguinal Hernia with Polypropylene Mesh Description of Procedure:

Introduction

After satisfactory endotracheal inhalation anesthesia was obtained, the patient's abdomen was prepped and draped in the usual fashion, after which CO2 pneumoperitoneum was instilled through a 10 mm Innerdyne trocar placed cephalad to the umbilicus at 4 L/min flow with pressures equal to or less than 17 mmHg to a total of 4.5 liters. A 45 degree angle laparoscope was introduced. General examination of the abdomen revealed findings as listed above.

Step 1: Under direct vision, 5 mm and 12 mm trocars were placed in the right and left mid abdomen respectively. (FIG. 1, 1a-1e)

Step 2: The patient was placed in Trendelenburg position. A curvilinear flap was developed in the right inguinal area using Everest Medical bipolar curved scissors and forceps and bi-toothed biopsy forceps. FIG. 9, 9a-9c)

Step 3: As the flap was developed it allowed entry into the preperitoneal space, which was dissected from the line of Douglas above to Cooper's ligament below lateral to the internal ring and medial to the midline. (FIG. 10, 10a-10i)

Step 4: Once fully developed and the extraneous sac removed from the internal ring, a piece of polypropylene mesh measuring 6×5 inches was rolled up into a 10-11 mm trocar, popped down the 12 mm trocar and then into the preperitoneal space. This was unfurled over the inguinal-femoral area. (FIG. 11, 11a-11e)

Step 5: Held in place with staples. (FIG. 12, 12a-12e)

Step 6: Pressure was then reduced to 6 mmHg and the leaves of peritoneum reapproximated with closely placed staples. (FIG. 13, 13a-13j)

Conclusion

When this was completed, instruments were removed, the CO2 let out through open valves and external massage, the trocars removed, the deep tissue closed with interrupted 2-0 Vicryl suture to the fascia and subcutaneous tissue, the skin closed with continuous running 4-0 Vicryl with half inch Steri-Strips. Tegaderm dressings were applied, 0.25% Marcaine with epinephrine instilled in the puncture sites for postop pain relief and the procedure terminated. (End of Example 4)

The preceding examples are intended to be exemplary, and the present invention is not limited to the preceding examples.

Figure 15:
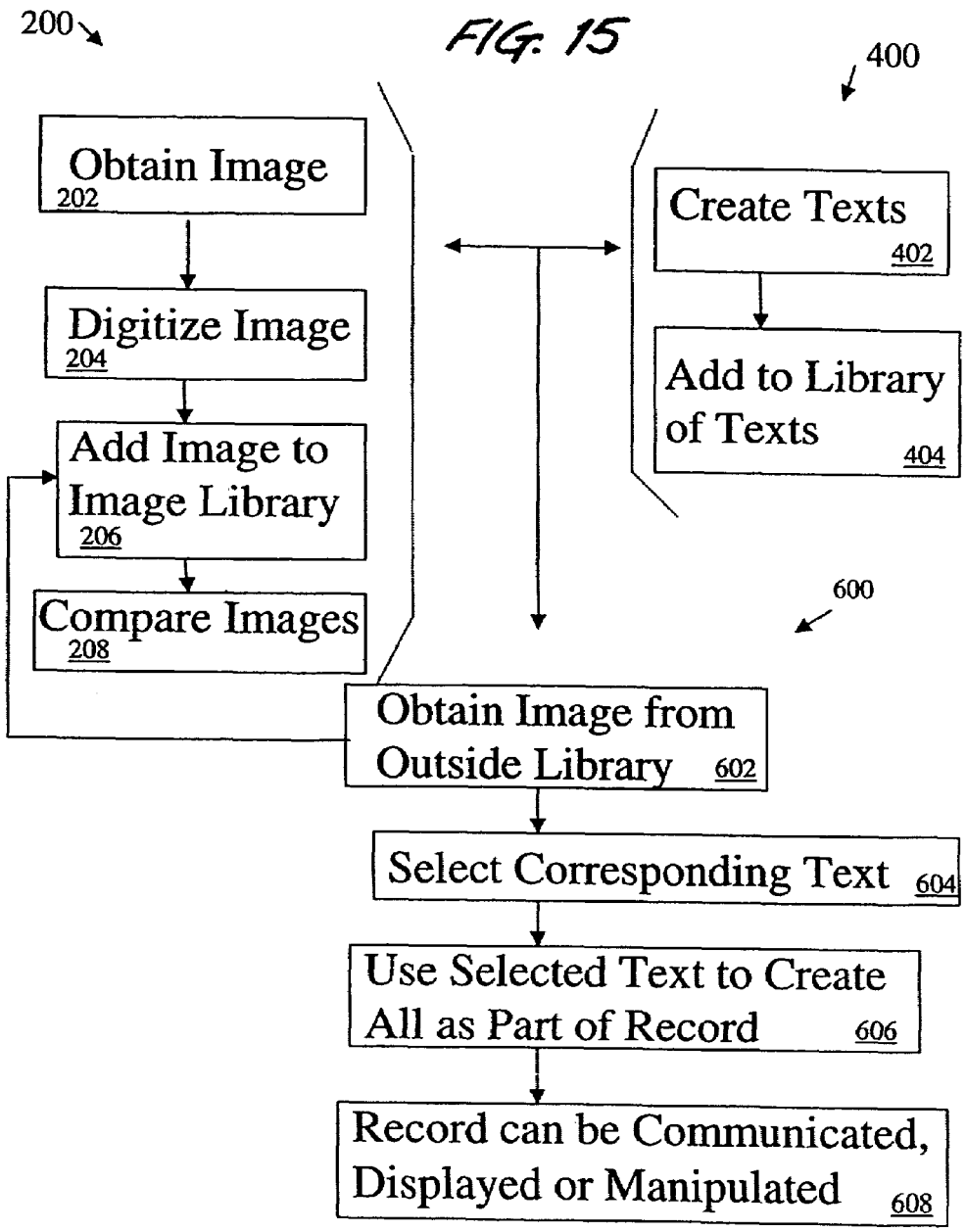
FIG. 15 depicts an embodiment of the process or method of the present invention.

FIG. 15 depicts one embodiment of the method, process and/or functional flow of the present invention. The images are obtained and stored in the image library, 200. First the image is obtained, 202, and then appropriately digitized, 204. The digitized images are then added to the image library 206 and compared to the images in the library, 208. Corresponding to the images or to groups of similar images (e.g. Figures) is the respective text descriptions of the steps and/or of the image, 400. The text is created, 402, and then added to a text library 404. Text creation, editing, and storage can be either a separate or concurrent function of the image processing.

The text and the images are combined together, 600, after the obtained image is compared to images from the image library 602. Similar images in the image library may be grouped together with a descriptive text associated with each grouping. Subgroups of the grouped images may be created to provide further descriptive detail to the step (e.g., the color of organ, the position of the organ, etc.). After the comparison of the images has been made and the obtained image is associated with a group and/or related subgroup, the obtained image is labeled with the corresponding text from the text library 604. The text that is selected from the text library is used to create a record 606 or part of a record. The record or portion there of that is created can then be communicated, displayed, or manipulated, 608.

The following are "stylized" descriptive texts based on the steps and images from the above examples. These stylized texts are examples of language which may be descriptive of the various steps, procedures, functions, physiology, physiological conditions, and the like generally typical of gallbladder and hernia procedures, respectively. The process outlined in FIG. 15 may be used to create a record comprising the following stylized steps. The text for the steps of the procedure may be set or read only; however, a doctor or other person creating a record may insert patient specific details in the introduction and conclusion of the record to account for problems, deviations or additions to the set-up or closing procedures.

Gallbladder (Stylized Text)

Step 1: The bitoothed biopsy forceps were used to grab the fundus of the gallbladder with upward retraction. (FIG. 1, 1a-1e)

Step 2: A 17 gauge pericardial needle was passed percutaneously into the gallbladder. Excess bile was aspirated and replaced with 60 cc of 50% Hypaque instilled in two separate aliquots of 50 and 10 cc each. At the end of the infusion of each of the two aliquots, x-rays were taken and examined in the operating room with the findings as listed above. The excess Hypaque was aspirated and the needle removed under direct vision. (FIG. 2, 2a-2c)

Step 3: A 5-mm and 12-mm trocar were placed in the right mid-abdomen. The patient was placed in reversed Trendelenburg position. (FIG. 3, 3a-3d)

Step 4: The gallbladder was grasped at the neck and dissected out from surrounding tissue. The gallbladder junction with the cystic duct was identified. The cystic duct was fully dissected away from the gallbladder and the cystic artery noted. (FIG. 4, 4a-4i)

Step 5: The cystic duct was dissected free, and clipped proximally and distally, divided. (FIG. 5, 5a-5f)

Step 6: The cystic artery was electrocoagulated with bipolar cautery. (FIG. 6, 6a-6c)

Step 7: The gallbladder was dissected off the liver bed with bipolar cautery. (FIG. 7, 7a-7g)

Step 8: The gallbladder was led out of the abdomen through the 12-mm trocar. (FIG. 8, 8a-8b)

Hernia (Stylized Text)
  Step 1: Under direct vision, 5-mm and 12-mm trocars were placed in the right and left midabdomen, respectively. FIG. 1, 1a-1e)
  Step 2: The patient was placed in the Trendelenburg position. A curvilinear flap was developed using Everest Medical curved scissors and forceps and bitoothed biopsy forceps. (FIG. 9, 9a-9c)
  Step 3: The space was dissected from the line of Douglas above to Cooper's ligament below. (FIG. 10, 10a-10i)
  Step 4: A piece of polypropylene mesh was tightly rolled up and placed into the preperitoneal space. This was unfurled over the inguinal femoral area. (FIG. 11, 1a-1e)
  Step 5: The mesh was stapled in place. (FIG. 12, 12a-12e)
  Step 6: Pressure was then reduced and the leaves of the peritoneum then reapproximated with closely placed staples. (FIG. 13, 13a-13j)

In one embodiment, the apparatus of the present invention may further comprise an input/output device 112 located in or just outside an operating room. In this example, a surgeon could perform a procedure while it is being filmed and while the film (image) is processed to produce a record in accordance with the present invention. Upon finishing the procedure and leaving the operating room, the record could be accessed in hard or electronic form by the surgeon, e.g., at a terminal 112 outside the operating room. The surgeon could then immediately review the text, edit it if desirable or necessary and sign it. In some embodiments, the signature may be electronic, and the record may be immediately placed in an electronic chart or patient record.

One example of using the apparatus and methods of the present invention in fields other than medicine is their use in mass or batch manufacturing or production of parts. In this example, the parts are typically subjected to a number of steps or processes to provide a raw, or stock, material with selected features. Images of the steps, and the part during and/or after the steps, can be captured. These images, which may be digital initially or digitized, may be stored in a library of images, and/or may be immediately or at a later time compared to other images in the library or to real time images or the process as it occurs. This comparison could be used, for example, to assess the repeatability of the process, and/or that the finished parts meet required tolerances. Stored images from the library could be used for educational purposes, e.g., to train production line workers, and/or for assessments of the cost and/or time efficiency of the process. The images also could be used to create a record of production, required tolerances, standard operation procedure and/or testing. For example, images could be compared to assess tolerances of finished parts and, if an "out-of-tolerance" part or feature is detected, a warning message or text could be produced and recorded and/or sent to a monitoring location; the images of the steps could be used to trigger a written standard operating procedure and/or portions thereof; and/or the images could be used to trigger a written or textual production and/or quality control record. Similarly, the methods and apparatus of the present invention could be used in assembly line settings, wherein a final product is built or assembled.

Another example of using the apparatus and methods of the present invention in fields other than medicine is their use in athletic or sports training in improving techniques, for example, in improving a golf swing. A golf swing involves various body and club positions and movements. A person trying to improve his or her golf swing may stand at a tee with his club and swing at a ball while a camera, video camera or the like photographs the golfer. The camera obtains images of various parts and aspects of the golfer's swing, positioning, and movement. Such images may be saved or stored in an image library, which may thus comprise images and/or groups of similar images of the various golfers and/or images of various golf swings, including stylized or ideal golf swings. A processing unit could digitize the obtained images from the golfer's swing and compare the images obtained to the images in the library, for example, to the ideal swing images. The obtained images may then identified, and/or added to the images library, and a text from a text library, may be added to create a report identifying, for example, what is incorrect with the golfer's swing and suggestions on how to correct it.

Referring to FIGS. 16 and 17, one example would be that the camera could focus on the position of the club head on the golfer's back swing. The images in the library would have various images of an "open" and "closed" back swing as depicted by the possible representative images in FIG. 16. The obtained image would be compared to the images in the image library and identified as either "open" or "closed". FIG. 17 shows representative figures of possible images for the library of images. If the back swing is "closed" a text statement would be added to the report identifying the golfer's back swing as "closed", stating the problems of having a "closed" back swing, stating how to change the back swing to "open", and how an "open" back swing should improve their swing. The report may be available in hard or electronic form, and may be available to the golfer and/or a teaching pro.

The methods and apparatus of the present invention may be used for any medical treatment or surgical procedure, and may be used in fields other than medicine. Suitable computer and/or microprocessing equipment and systems, including suitable software, may be used to accomplish the methods of the present invention, along or in conjunction with suitable image capturing and processing equipment or systems and communication systems. In some embodiments, the present invention may comprise a dispersed library of information, i.e., there is no "central station," central library, central server or central repository, but rather a substantially instantaneous communication or flow of information over the internet or the like. The present invention encompasses taking, transmitting and processing digital images, wherein the digital images can be placed into a digital library of images directly. It encompasses a digital library of digital or digitized images and texts, wherein the digital library may be accessed and/or manipulated from a central and/or one or more remote locations.

The present invention may be embodied in other specific forms without departing from the essential spirit or attributes thereof, and it may be used in applications outside the medical field. Described embodiments should be considered in all respects as illustrative, not restrictive.

What is claimed is:

1. A device for providing a text related to an image in a record, comprising:
    a microprocessor;
    a library of stored images drawn from previously produced records, wherein generally similar stored images depicting similar elements across different previously produced records are grouped together; and
    a library of stored texts, wherein each of the stored texts is associated with one group of stored images;
    wherein, upon receipt of a new image, the microprocessor compares the new image to the stored images, and selects for inclusion in the record the stored text associated with the group of the stored image that is most similar to the new image.

2. The device of claim 1, wherein the new image, stored images and stored texts are digital.

3. The device of claim 2, wherein the microprocessor uses digital image recognition to identify the one of the stored images that is most similar to the new image.

4. The device of claim 1, wherein, when no stored image is similar to the new image, the microprocessor generates a signal to indicate that no match has been identified for the new image.

5. A device for producing a text for use in a record concerning a procedure, comprising:
  a library of stored images drawn from past procedures, wherein generally similar stored images depicting similar steps or actions from different past procedures are grouped together;
  a library of stored texts, each of the groups of stored images being associated with at least a portion of one of the stored texts;
  a microprocessor,
  wherein, upon receipt of a new image, the microprocessor compares the new image to the stored images,
  and, based on the comparison, selects for inclusion in the record concerning a procedure the portion of one of the stored texts associated with the group of the stored image that is most similar to the new image into the record concerning a procedure.

6. The device of claim 5, wherein the procedure is a surgical procedure and the past procedures are past surgical procedures.

7. The device of claim 5, wherein the new image is compared with the stored images using digital image recognition.

8. The device of claim 5, wherein the new image is a real-time image.

9. An apparatus for producing a record comprising:
  means for storing a plurality of images and a plurality of texts from previous records, and grouping generally similar stored images depicting similar elements from separate previous records, at least a portion of each stored text being associated with one of the groups;
  means for comparing a new image to the stored images using digital image recognition to identify one or more stored images that are most similar to the new image; and
  means for creating a record by including the stored text associated with the group of the identified stored image in the record.

10. The apparatus of claim 9, wherein the stored text included in the record is descriptive of the new image.

11. The apparatus of claim 9, further comprising means for digitizing the images.

12. The apparatus of claim 9, further comprising means for communicating the images and texts.

13. The apparatus of claim 9, wherein the images depict aspects of medical procedures.

14. A method of providing a medical record comprising the steps of:
  capturing one or more library video images of a medical procedure to form a group of library video images depicting similar steps of similar medical procedures;
  processing the group of library video images to provide a group of library digital images corresponding to the library video images;
  associating a text description with the group of library digital images;
  capturing an outside video image of an outside medical procedure and processing the outside video image to provide an outside digital image; and
  comparing the library digital image and the outside digital image, wherein the text description associated with the group comprising the library digital image most similar to the outside digital image is selected for inclusion in a medical record wherein each of the above listed steps is performed with a processor.

15. The method of claim 14, wherein a plurality of grouped library video images and respective grouped library digital image signals and text descriptions are captured, processed, and associated.

16. The method of claim 15, wherein the grouped library digital image signals and text descriptions comprise an electronically accessible database.

17. A method of creating a record comprising the steps of:
  forming groups of library images, each group depicting a portion of a procedure;
  forming a group of library texts describing the procedure, wherein each of the library texts forming the group of library texts corresponds to one of the portions of a procedure;
  providing an outside image of a procedure;
  comparing the outside image to the groups of library images;
  selecting an image or group of images from the library images that are most similar to the outside image;
  selecting the library text corresponding to the portion of the procedure corresponding with the selected library image; and
  inserting the selected library text into a document to create a record wherein each of the above listed steps is performed with a processor.

18. The method of claim 17, wherein the library images and the library texts are digital.

19. The method of claim 18, wherein the outside image is digital.

20. The method of claim 19, wherein the steps of selecting an image and selecting the library text are accomplished by a microprocessor.

21. The method of claim 17, wherein the most similar library image is selected using digital image recognition.

22. The method of claim 17, wherein the record created is a medical record.

23. A computer-readable medium encoded with a computer program code for providing a medical record, the program code causing a computer to perform the steps of:
  creating a library of stored images, wherein generally similar stored images depicting the same elements from different medical records are grouped together;
  creating a library of stored texts, wherein each of the stored texts is associated with one of the groups of stored images;
  receiving a new image;
  comparing the new image to the stored images using digital image recognition to identify the one or more stored images that are most similar to the new image; and
  when the most similar one or more stored images are identified, selecting for inclusion in a medical record the stored text associated with the group of the identified stored image.

24. The method of claim 23, wherein the new image, stored images and stored texts are digital.

25. The method of claim 23, further comprising the step of:
  generating a signal to indicate that no match has been identified for the new image when none of the stored images are similar to the new image.

26. A method of providing a medical record, comprising:
  capturing a video image of a medical procedure;
  processing the video image to provide a new digital image signal;

comparing the new digital image signal to a digital image signal from at least one previously captured video image associated with a group, wherein the group is associate with a previously created text description;

selecting the previously created text description to become at least a portion of the medical record if the new digital image signal is similar to the at least one digital image signal from a previously captured video image; and providing an indication of dissimilarity if the new digital image signal is not similar to the digital image signal from any of the previously captured video images wherein each of the above listed steps is performed with a processor.

27. The method of claim 26, wherein the previously captured video image is from a previously performed medical procedure.

28. The method of claim 26, wherein the indication of dissimilarity is a warning signal.

29. The method of claim 26, wherein the at least one previously captured video image and previously created text are stored in an electronically accessible database, and further comprising:

storing the new digital video image and a text description of the new digital video image in the database.

30. The device of claim 1, wherein the microprocessor generates the record.

* * * * *